(12) United States Patent
Ishikawa et al.

(10) Patent No.: US 10,583,217 B2
(45) Date of Patent: Mar. 10, 2020

(54) IMPLANT AND METHOD FOR PRODUCING IMPLANT

(71) Applicant: NIPPON PISTON RING CO., LTD., Saitama, Saitama (JP)

(72) Inventors: Yoshiki Ishikawa, Saitama (JP); Yuki Kimura, Saitama (JP); Takasumi Kubo, Saitama (JP); Hiroshi Matsushima, Saitama (JP); Takashi Kawabata, Saitama (JP); Toshio Nagase, Ibaraki (JP)

(73) Assignee: NIPPON PISTON RING CO., LTD. (JP)

( * ) Notice: Subject to any disclaimer, the term of this patent is extended or adjusted under 35 U.S.C. 154(b) by 235 days.

(21) Appl. No.: 15/720,020

(22) Filed: Sep. 29, 2017

(65) Prior Publication Data
US 2018/0093012 A1 Apr. 5, 2018

(51) Int. Cl.
*A61L 27/06* (2006.01)
*A61B 17/80* (2006.01)
(Continued)

(52) U.S. Cl.
CPC ............ *A61L 27/06* (2013.01); *A61B 17/725* (2013.01); *A61B 17/7208* (2013.01); *A61B 17/744* (2013.01); *A61B 17/809* (2013.01); *A61B 17/86* (2013.01); *A61F 2/3094* (2013.01); *A61F 2/3609* (2013.01); *A61L 27/50* (2013.01); *A61L 31/022* (2013.01); *A61L 31/14* (2013.01); *A61B 17/8061* (2013.01); *A61B 2017/00526* (2013.01); *A61B 2017/00862* (2013.01); *A61B 2017/00867* (2013.01); *A61F 2002/30014* (2013.01); *A61F 2002/30092* (2013.01); *A61F 2002/30975* (2013.01);
(Continued)

(58) Field of Classification Search
CPC ........ A61L 27/50; A61L 27/06; A61B 17/725
See application file for complete search history.

(56) References Cited

U.S. PATENT DOCUMENTS

| | | | | |
|---|---|---|---|---|
| 4,592,890 A * | 6/1986 | Burnett | ................. | C22C 19/058 420/442 |
| 7,264,665 B2 * | 9/2007 | Hoescheler | .......... | A61K 6/0835 106/35 |
| 2005/0158693 A1 * | 7/2005 | Prasad | ................. | A61K 6/0205 433/207 |
| 2011/0270407 A1 * | 11/2011 | Cougoulic | ............. | A61K 6/033 623/23.61 |

(Continued)

FOREIGN PATENT DOCUMENTS

| | | |
|---|---|---|
| JP | 2003-500156 A | 1/2003 |
| JP | 2012-504027 A | 2/2012 |

(Continued)

*Primary Examiner* — Christian A Sevilla
(74) *Attorney, Agent, or Firm* — Harness, Dickey & Pierce, P.L.C.

(57) ABSTRACT

There is provided an implant that is safe for the living body. An angular plate as the implant includes a bone supporting plate part and a blade part. The blade part is integrally formed with the bone supporting plate part, and extends from one end of the bone supporting plate part at a predetermined angle α (0°<α<180°) relative to the bone supporting plate part. The angular plate is formed from a titanium-tantalum-based alloy containing tin. The angular plate is preferably formed from a titanium-tantalum-based alloy containing tin in which a Young's modulus is decreased by increasing the reduction ratio thereof.

23 Claims, 17 Drawing Sheets

(51) Int. Cl.
    *A61B 17/86*     (2006.01)
    *A61B 17/72*     (2006.01)
    *A61F 2/36*     (2006.01)
    *A61L 27/50*     (2006.01)
    *A61L 31/14*     (2006.01)
    *A61L 31/02*     (2006.01)
    *A61F 2/30*     (2006.01)
    *A61B 17/74*     (2006.01)
    *A61B 17/00*     (2006.01)

(52) U.S. Cl.
    CPC ............... *A61F 2310/00023* (2013.01); *A61F 2310/00119* (2013.01); *A61F 2310/00131* (2013.01); *A61L 2400/16* (2013.01); *A61L 2430/02* (2013.01)

(56) References Cited

U.S. PATENT DOCUMENTS

2012/0183923 A1*   7/2012   Takagi ................ A61C 8/0012
                                                               433/173
2012/0265165 A1* 10/2012   Bucknall ................ A61L 27/26
                                                                604/500
2013/0309518 A1   11/2013   Takeguchi et al.

FOREIGN PATENT DOCUMENTS

| | | |
|---|---|---|
| JP | 2012-196463 A | 10/2012 |
| JP | 5855588 B2 | 2/2016 |
| WO | WO-2000-072770 A1 | 12/2000 |
| WO | WO-2010-037038 A2 | 4/2010 |

* cited by examiner

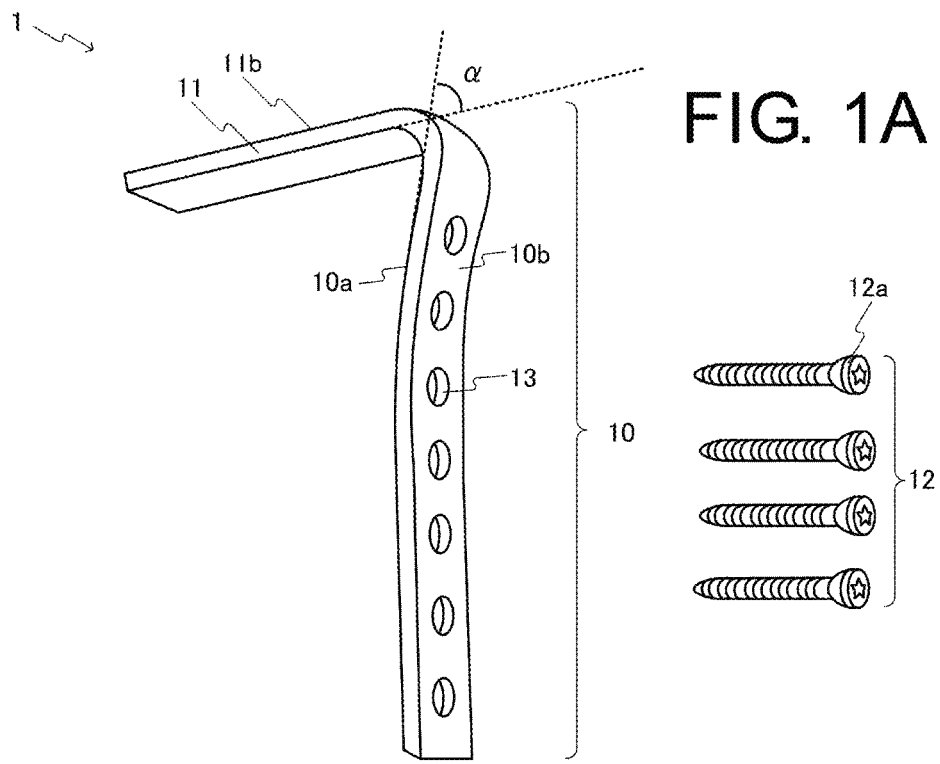
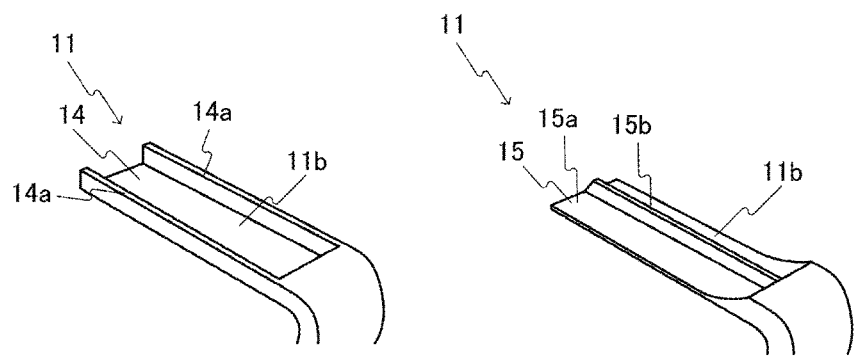

Fig. 4A
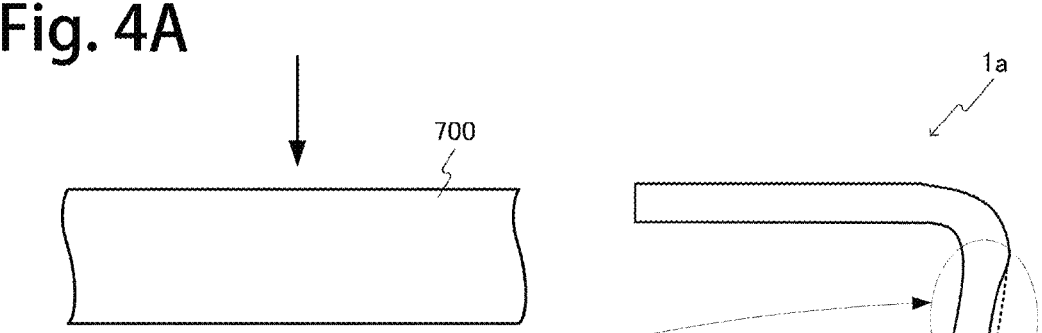
Fig. 4B
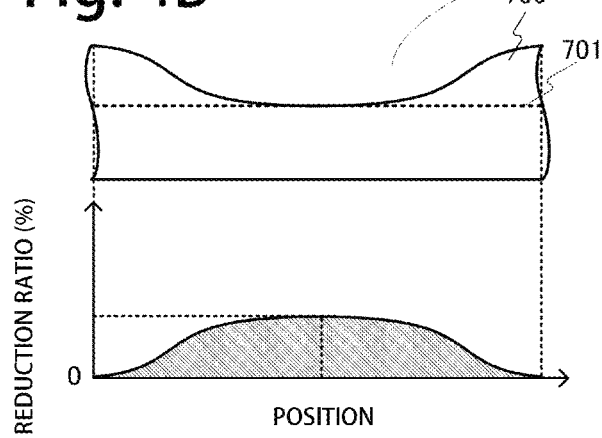
Fig. 4D
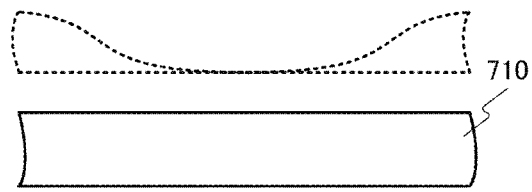
Fig. 4C

IMPLANT AND METHOD FOR PRODUCING IMPLANT

BACKGROUND OF THE INVENTION

1. Field of the Invention

The present invention relates to an implant and a method for producing the same.

2. Description of the Related Art

A nickel-titanium-based alloy is a shape-memory alloy. The nickel-titanium-based alloy can be readily deformed at a temperature that is equal to or lower than a transformation temperature range. Further, the original shape before the deformation of the deformed nickel-titanium-based alloy can be recovered at a temperature that is equal to or higher than the transformation temperature range. Attention is being given to such properties of the nickel-titanium-based alloy, and in recent years, the nickel-titanium-based alloy has been often used as a material for an implant used in orthopedics for enhancement of a fractured bone. For example, an intramedullary nail for enhancement of a fractured bone that is formed from the nickel-titanium-based alloy has been proposed (for example, see Patent Literature 1). Further, a spinal rod configured to extend along a part of the spinal column that is formed from the nickel-titanium-based alloy (for example, nitinol) has been proposed (for example, see Patent Literature 2). Moreover, an implant that fixes a rod-shaped member to be embedded in a bone fracture area with a screw and that is formed from the nickel-titanium-based alloy (for example, nitinol) has been proposed (for example, see Patent Literature 3).

The applicant of the present application has proposed a titanium alloy including tantalum (Ta) and tin (Sn) with the balance being titanium (Ti) and unavoidable impurities as a biocompatible material (for example, see Patent Literature 4).

CITATION LIST

Patent Literature

Patent Literature 1: Japanese Patent Application Laid-Open No. 2012-196463
Patent Literature 2: International Publication No. WO2000/072770
Patent Literature 3: International Publication No. WO2010/037038
Patent Literature 4: Japanese Patent No. 5855588

SUMMARY OF THE INVENTION

Since nickel may cause allergies in a living body, it is preferable that an implant be formed from a material containing no nickel from the viewpoint of safety of the living body.

The nickel-titanium-based alloy is highly magnetic. Therefore, during diagnosis by MRI with an implant formed from the nickel-titanium-based alloy left in a living body, the implant may generate heat due to a magnetic field generated by an MRI device.

Further, the nickel-titanium-based alloy has a low X-ray absorptivity. Therefore, when the position of the implant is checked from a radiograph for follow up on bone fracture or the like, it may take a long time to find the implant.

The present invention has been made in view of the aforementioned problems. It is an object of the present invention to provide an implant that is safe for the living body, and a method for producing the implant.

In order to solve the aforementioned problems, an implant of the present invention includes at least partially an alloy containing titanium, tantalum, and tin, wherein the alloy contains 15 at % to 27 at % of tantalum and 1 at % to 8 at % of tin, relative to the entire amount thereof taken as 100 at %, with the remaining part being titanium and unavoidable impurities.

The implant of the present invention at least partially includes an elastically deforming part that is elastically deformable.

In the implant of the present invention, the elastically deforming part includes a part having an increased reduction ratio as compared with other parts.

The implant of the present invention has a hardened part having an increased hardness as compared with other parts. The hardened part is formed by subjecting the part to a heat treatment.

In the implant of the present invention, at least a part of the alloy is subjected to an aging treatment.

In the implant of the present invention, the alloy is subjected to the aging treatment for a holding time of 30 hours or less.

The implant of the present invention repairs a bone.

The implant of the present invention includes a part to be attached to the outer periphery of the bone. The part to be attached to the outer periphery of the bone is formed in a plate shape.

In the implant of the present invention, the part to be attached to the outer periphery of the bone is fixed on the outer periphery of the bone with a screw member.

The implant of the present invention includes a part to be attached to the inside of the bone.

The implant of the present invention includes a part of penetrating insides of parts of a fractured bone.

In the implant of the present invention, the part of penetrating the insides of the parts of the fractured bone is formed in a screw shape.

The implant of the present invention is at least partially formed in a screw shape.

The implant of the present invention is at least partially formed in a bar shape.

According to a method for producing an implant of the present invention, the implant is produced from a material including an alloy containing titanium, tantalum, and tin.

The method for producing an implant of the present invention includes a deformation treatment step of deforming at least a part of the material.

The method for producing an implant of the present invention includes an aging treatment step of subjecting at least a part of the material or at least a part of an intermediate that is formed during a process of producing the implant to an aging treatment.

In the method for producing an implant of the present invention, the alloy is subjected to the aging treatment for a holding time of 30 hours or less.

The method for producing an implant of the present invention includes a solution treatment step of subjecting at least a part of the material or at least a part of the intermediate that is formed during the process of producing the implant to a solution treatment.

The method for producing an implant of the present invention includes the solution treatment step of subjecting at least a part of the material or at least the part of the intermediate that is formed during the process of producing the implant to the solution treatment, wherein the solution treatment step is performed after the deformation treatment step.

In the deformation treatment step of the method for producing an implant of the present invention, the reduction ratio of apart of the material is changed to a first reduction ratio, and the reduction ratio of at least a part of the rest of the material is changed to a second reduction ratio that is higher than the first reduction ratio.

In the method for producing an implant of the present invention, the material comprises two ingots including an alloy containing titanium and tantalum, the deformation treatment step includes a first ingot deformation treatment step of changing the reduction ratio of at least a part of one of the ingots to a first reduction ratio and a second ingot deformation treatment step of changing the reduction ratio of at least a part of the other ingot to a second reduction ratio that is higher than the first reduction ratio, the implant includes at least a first part and a second part, the first part is formed from the ingot that has been subjected to the first ingot deformation treatment step, and the second part is formed from the ingot that has been subjected to the second ingot deformation treatment step.

In the method for producing an implant of the present invention, the implant is configured such that apart where the reduction ratio is changed in the deformation treatment step forms the elastically deforming part that is elastically deformable.

Effects of the Invention

The implant of the present invention can exert an excellent effect that is safe for the living body. The method for producing an implant of the present invention can exert an excellent effect in which the implant safe for the living body can be produced.

BRIEF DESCRIPTION OF THE DRAWINGS

FIGS. 1A, 1B, and 1C are views illustrating an angular plate and screw members that are implants in a first embodiment of the present invention where FIG. 1A is a perspective view of the angular plate and the screw members that are the implants in the first embodiment, FIG. 1B is a perspective view illustrating one example of a structure of a blade part in the angular plate, and FIG. 1C is a perspective view illustrating another example of a structure of the blade part in the angular plate;

FIGS. 4A, 4B, 4C, and 4D are views illustrating a method for producing a non-contact part in the angular plate as the implant in the first embodiment;

FIG. 6A is a graph showing a relationship between the holding time and the hardness in an aging treatment at 450° C., FIG. 6B is a graph showing a relationship between the holding time and the hardness in an aging treatment at 500° C., and FIG. 6C is a graph showing a relationship between the holding time and the hardness in an aging treatment at 500° C. after a solution treatment of the Ti-23Ta-3Sn alloy (the alloy is held at 850° C. for 3 hours);

DETAILED DESCRIPTION OF THE PREFERRED EMBODIMENTS

Figure 2A:
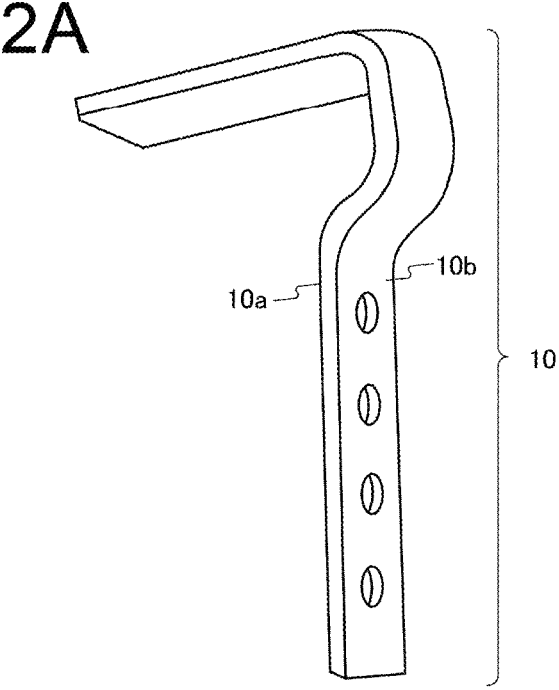
FIGS. 2A and 2B are views illustrating a modification of a bone supporting plate part in the angular plate as the implant in the first embodiment.

Hereinafter, embodiments of the present invention will be described with reference to accompanying drawings. In each drawing, some parts are approximately omitted or simplified for easy understanding. The shape and dimensional ratio in each drawing are not limited to those in the drawings.

1. First Embodiment 1-1. General Configuration

An angular plate 1 that is an implant in a first embodiment of the present invention will be described below with reference to FIGS. 1A, 1B, 1C, 2A, and 2B. The angular plate 1 is a device for fixing a bone fracture area, and includes a bone supporting plate part 10 and a blade part 11.

The bone supporting plate part 10 is formed in a substantially plate shape. One plane of the bone supporting plate part 10 in the thickness direction is an inner surface 10a of the bone supporting plate part 10. Another plane of the bone supporting plate part 10 in the thickness direction is an outer surface 10b of the bone supporting plate part 10. The inner surface 10a of the bone supporting plate part 10 is a surface to come into contact with the bone, as described below.

Figure 2B:
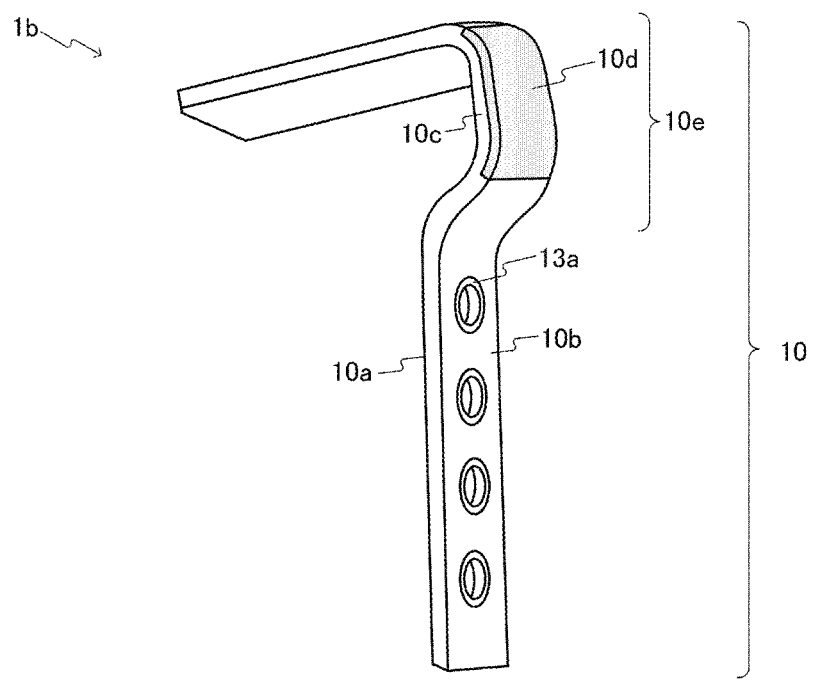

As shown in FIG. 1A, the bone supporting plate part 10 extends substantially linearly and curves toward the outer surface 10b side of the bone supporting plate part 10 at any point. In FIG. 1A, the bone supporting plate part 10 gently curves toward the outer surface 10b side of the bone supporting plate part 10 at any point. However, the bone supporting plate part 10 is not limited to this configuration. For example, the bone supporting plate part 10 may be an aspect in which the bone supporting plate part 10 bents toward the outer surface 10b side of the bone supporting plate part 10 at any point into an L shape as shown in FIGS. 2A and 2B.

The bone supporting plate part 10 has a plurality of holes 13 that each penetrate the bone supporting plate part 10 in the thickness direction of the bone supporting plate part 10. The holes 13 are arranged in a line at predetermined intervals in the longitudinal direction of the bone supporting plate part 10. Each of a plurality of screw members 12 are allowed to pass through each of the holes 13.

The holes 13 are each in a shape engageable with a head 12a of each of the screw members 12. Each of the screw members 12 is inserted into each of the holes 13 in a direction from the outer periphery 10b side toward the inner periphery 10a side of the bone supporting plate part 10 and the holes 13 are each engaged with each of the heads 12a. In this case, movement of the screw members 12 toward the inner periphery 10a side beyond engagement is restricted.

As shown in FIG. 1A, the blade part 11 is integrally formed with the bone supporting plate part 10. However, the blade part 11 is not limited to the integral configuration. The bone supporting plate part 10 and the blade part 11 may be linked with each other as separate members. The blade part 11 extends from one end of the bone supporting plate part 10 (herein, from one end on a curved or bent side) at a predetermined angle α (0°<α<180°) relative to the bone supporting plate part 10. In this case, a side of which the blade part 11 faces to the bone supporting plate part 10 is defined as an inside, and a side opposite to the aforementioned side is defined as an outside.

The blade part 11 has a band-shaped plate 14 capable of being inserted in or penetrating a bone. Specifically, the blade part 11 has a structure in which a stand part 14a is provided vertically on the outer surface 11b side of the plate 14 at both ends of the plate 14 in the widthwise direction, as shown in FIG. 1B. In this case, the cross section of the blade part 11 in a direction parallel to the widthwise direction is in a substantially C shape.

The blade part 11 is not limited to the aforementioned structure. For example, the blade part 11 may have a structure in which a projection part 15b is provided on a plate surface 15a that is on the outer surface 11b side in the thickness direction of the plate 15, in a direction vertical to the plate surface 15a, as shown in FIG. 1C. The projection part 15b extends along the longitudinal direction of the plate 15 at a center in the widthwise direction of the plate 15.

When the angular plate 1 has high rigidity, the angular plate 1 may damage the living body including the bone due to a force applied to the bone fracture area that is fixed by the angular plate 1. In contrast, when the angular plate 1 is elastically deformable, by elastic deformation of the angular plate 1, the angular plate 1 can prevent occurrence of damage in the living body including the bone due to a force applied to the bone fracture area that is fixed by the angular plate 1. Therefore, it is preferable that the angular plate 1 at least partially have an elastically deforming part that is elastically deformable.

Examples of a part corresponding to the elastically deforming part may include the whole angular plate 1, the bone supporting plate part 10, the blade part 11, a junction between the bone supporting plate part 10 and the blade part 11, a part thereof, and a combination thereof. The elastically deforming part may be formed from an elastically deformable material.

It is preferable that at least a part of the angular plate 1 be formed from a material having moderately low elastic limit. In this case, the part of the angular plate 1 (for example, the bone supporting plate part 10) can be plastically deformed with ease.

1-2. Attachment of Angular Plate to Bone Fracture Area

Figure 3:
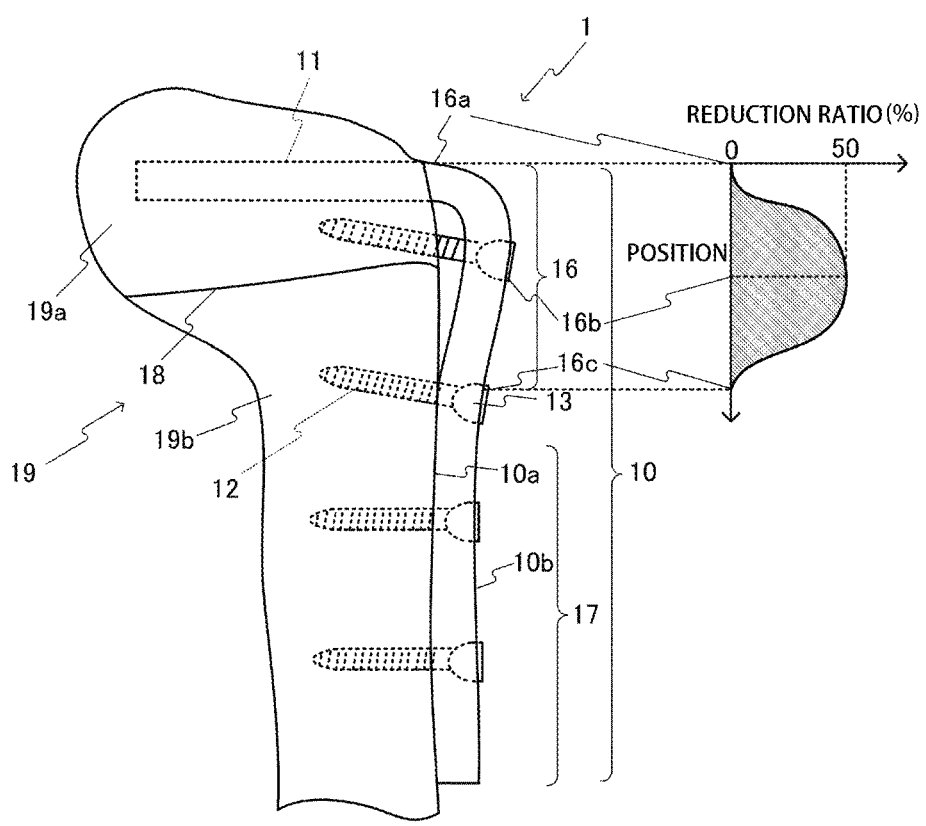
FIG. 3 is a view illustrating a state where the angular plate as the implant in the first embodiment is attached to a bone fracture area.

Next, a procedure of attaching the angular plate 1 to a bone fracture area when a bone 19 is fractured into a bone part 19a in the vicinity of the distal and a bone part 19b on a side of a main body will be described with reference to FIG. 3. In attachment of the angular plate 1 to the bone fracture area, the bone supporting plate part 10 is disposed over a bone fracture part 18 that represents a surface of fractured part of the bone 19 so that the inner surface 10a of the bone supporting plate part 10 partially comes into contact with an outer periphery of the bone part 19b, as shown in FIG. 3. In this case, the bone supporting plate part 10 curves outward in the vicinity of an end part connecting to the blade part 11. Therefore, a non-contact part 16 is formed. The non-contact part 16 is a part in which the outer periphery of the bone part 19b is apart from the inner surface 10a of the bone supporting plate part 10 without being in contact with each other (the non-contact part may also be referred to as a curved part). In order to decrease the area of the non-contact part 16, the bone supporting plate part 10 may be deformed into a shape corresponding to the shape of the outer periphery of the bone part 19b. In this case, a force exceeding the elastic limit is applied to the bone supporting plate part 10.

On the other hand, the blade part 11 is inserted in the bone part 19a that is one part of the bone separated at the bone fracture part 18 into two parts. The screw members 12 are then threaded into the bone part 19b through the holes 13 from the outer surface 10b side of the bone supporting plate part 10, and threadedly engaged with the bone part 19b. Some of the screw members 12 may be threaded into the bone part 19a. When the bone supporting plate part 10 is configured as the elastically deforming part, the bone supporting plate part 10 can be elastically deformed so as to be along the outer periphery of the bone part 19b by pushing the bone supporting plate part 10 onto the outer periphery of the bone part 19b by the screw members 12. When the bone supporting plate part 10 is deformed so as to exceed the elastic limit and the angle α between the blade part 11 and the bone supporting plate part 10 is set to be slightly smaller than an angle during actual connection, the non-contact part 16 or the like can be elastically deformed during fixation and function as a biasing member. Thus, the bone part 19a can be pushed onto the bone part 19b by the blade part 11. Specifically, the bone fracture area of the bone 19 is fixed by the angular plate 1 so that the bone parts 19a and 19b into which the bone is separated at the bone fracture part 18 are connected to each other. As described above, the angular plate 1 is used to achieve connection in the bone fracture area of the bone 19.

1-3. Material for Angular Plate

Next, a specific material for the angular plate 1 will be described. The angular plate 1 is formed from a titanium-tantalum (Ti—Ta)-based alloy containing at least titanium (Ti) and tantalum (Ta).

An alloy forming the angular plate 1 is not particularly limited as long as it is the alloy containing at least titanium and tantalum. The alloy may further contain an element other than titanium and tantalum. For example, the alloy forming the angular plate 1 may be an alloy containing titanium, tantalum, and tin (Sn). In this case, favorable mechanical properties can be obtained.

Specifically, it is preferable that a titanium-tantalum-based alloy containing tin (Sn) in the embodiment of the present invention contain 15 at % or more and 27 at % or less of tantalum and 0 at % or more and 8 at % or less of tin, relative to the entire amount taken as 100 at %, with the balance being titanium and unavoidable impurities. Such an alloy can have more favorable mechanical properties, that is, high tensile strength, low Young's modulus, and moderate elastic limit. In addition, high biocompatibility can be achieved.

The lower limit of the content of tin (Sn) may be 0 at %, as described above. This is because a titanium alloy having mechanical properties (Young's modulus, tensile strength, and elastic deformation strain) required for the angular plate 1 can be obtained even without addition of Sn when the content of Ta is 15 at % or more.

In order to improve the mechanical properties, it is preferable that the titanium-tantalum-based alloy contain tin (Sn) from the viewpoint of super-elastic effect of the titanium-tantalum-based alloy. This is because tin (Sn) suppresses deposition of an ω phase that causes an increase in Young's modulus and has a function of enhancing the super-elastic effect of the titanium-tantalum-based alloy. This super-elasticity makes it possible to appropriately deal with unintended deformation. When the alloy is applied to the angular plate 1, the angular plate 1 appropriately allows a case where the bone parts 19a and 19b in treatment are forcibly separated due to any impact in daily living, and subsequently makes it possible to naturally recover the original fixation state from the separated state. Therefore, it is preferable that the titanium-tantalum-based alloy contain tin (Sn). In order to sufficiently exert the above-described ω phase suppressing function, the content of Sn is preferably 1 at % or more relative to the entire amount of the titanium alloy taken as 100 at %.

In the titanium-tantalum-based alloy containing tin (Sn), the amounts of eluted metal ions such as Ti, Ta, and Sn as constituent elements are very small. In addition, the titanium-tantalum-based alloy exhibits excellent corrosion resistance, low cytotoxicity, and high biocompatibility, is non-magnetic, and has high elasticity, moderate rigidity, and high workability. The alloy that is non-magnetic means that the alloy is unlikely to be magnetized by an external magnetic field. Therefore, the alloy is unlikely to adversely affect medical devices (such as MRI) that should avoid magnetism. Specifically, the titanium-tantalum-based alloy containing tin (Sn) is a titanium-tantalum-based alloy having lower cytotoxicity, and excellent magnetic properties, corrosion resistance, mechanical properties, and workability as compared with the conventional titanium alloy.

1-3-1. Young's Modulus of Material for Angular Plate

Figure 5:
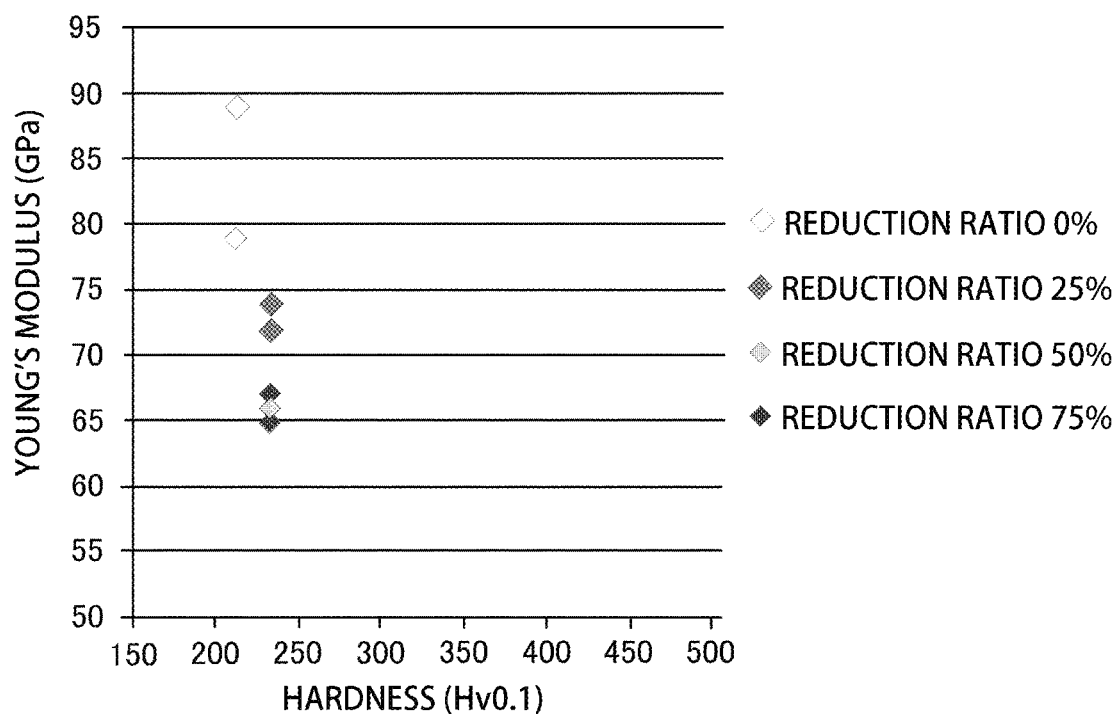
FIG. 5 is a graph showing a relationship between the hardness and the Young's modulus of a Ti-23Ta-3Sn alloy (titanium-tantalum-based alloy containing 23 at % of tantalum and 3 at % or less of tin, relative to the entire amount thereof taken as 100 at %, with the balance being titanium and unavoidable impurities: hereinafter the same is applied) in which the reduction ratio is 0%, 25%, 50%, or 75%.

A change in Young's modulus corresponding to a change in reduction ratio of the titanium-tantalum-based alloy containing tin (Sn) will be described with reference to FIG. 5. FIG. 5 shows the Young's modulus when the reduction ratio of the Ti-23Ta-3Sn alloy is 0%, 25%, 50%, or 75%. As shown in FIG. 5, when the reduction ratio of the Ti-23Ta-3Sn alloy is increased from 0% to 25% or from 25% to 50%, the Young's modulus is decreased. Therefore, it is considered that the Young's modulus of the titanium-tantalum-based alloy containing tin (Sn) is decreased with an increase in the reduction ratio of the alloy. On the other hand, the surface hardness is hardly changed. Therefore, the change in the reduction ratio does not adversely affect the fastening strength of the screw members 12.

In attachment of the angular plate 1 to the bone fracture area, it is preferable that the angular plate 1 have moderate flexibility and be formed so as to cause elastic deformation, as described above. Therefore, it is preferable that the angular plate 1 be formed from a titanium-tantalum-based alloy containing tin (Sn) in which a Young's modulus is decreased by increasing the reduction ratio. In particular, it is preferable that the angular plate 1 be formed from a titanium-tantalum-based alloy containing tin (Sn) in which a reduction ratio is 20% or more. It is more preferable that the angular plate 1 be formed from a titanium-tantalum-based alloy containing tin (Sn) in which a reduction ratio is 40% or more.

The reduction ratio of only a part of the titanium-tantalum-based alloy forming the angular plate 1 may be changed. Examples of the part of the angular plate 1 may include the bone supporting plate part 10, the blade part 11, the junction between the bone supporting plate part 10 and the blade part 11, a combination thereof, and a part thereof. As described above, the angular plate 1 can have apart that has low Young's modulus and flexibility and easily causes elastic deformation and a part having high rigidity.

1-3-2. Property of Contrast Radiography of Material for Angular Plate

An implant conventionally used in the body during bone fracture is formed from, for example, stainless steel such as SUS316L or a nickel-titanium (Ni—Ti)-based alloy that is a super-elastic alloy to achieve necessary mechanical properties (tensile strength, Young's modulus, elastic limit, etc.). However, such an implant is unlikely to be reflected in a X ray-radiograph since the material has a low X ray-absorptivity. In contrast, the titanium-tantalum-based alloy has properties such as high X-ray absorptivity (X-ray impermeability) in addition to tensile strength and Young's modulus that are the same degrees as those of the nickel-titanium-based alloy. This is because the titanium-tantalum-based alloy contains tantalum of which the atomic weight is large. Therefore, the angular plate 1 formed from the titanium-tantalum-based alloy has an excellent property of Contrast radiography during X ray-radiography.

1-3-3. Plastic Deformation of Material for Angular Plate

The titanium-tantalum-based alloy has moderately lower elastic limit than that of the nickel-titanium-based alloy. Therefore, the angular plate 1 formed from the titanium-tantalum-based alloy has strength and flexibility that are the same degrees as those of the nickel-titanium-based alloy, and in addition, can be plastically deformed as appropriate by bending. Accordingly, the bone supporting plate part 10 can be easily curved and deformed so as to be along the outer periphery of the bone 19.

1-3-4. Aging Treatment of Material for Angular Plate

Next, the hardness of the titanium-tantalum-based alloy containing tin (Sn) that is subjected to an aging treatment will be described with reference to FIGS. 6A, 6B, and 6C. The present inventor prepared four kinds of samples formed from the Ti-23Ta-3Sn alloy, which were subjected to an aging treatment at 450° C. and 500° C. Specifically, the samples were each placed in a vacuum furnace, and the aging treatment was performed for four different times of 1 hour, 3 hours, 7 hours, and 28 hours. The diameter of cross section of each of the samples was 13 mm, and the reduction ratio of each of the samples was 0%, 25%, 50%, or 75%. By a micro vickers hardness tester, the hardness of each of the samples having been subjected to the aging treatment was measured. A micro vickers hardness test was performed at 13 measurement points arranged at certain intervals (0.5 mm) from the outer peripheral edge toward the center in a cross section substantially orthogonal to the axial direction of each of the samples. The average of hardnesses at the 13 measurement points was obtained as a test result.

A case where the four kinds of samples were subjected to the aging treatment at 450° C. will be described with reference to FIG. 6A. In the sample in which the reduction ratio is 0%, as the holding time is longer, the hardness is higher. In the sample in which the reduction ratio is 0%, a gradient in which the hardness increases until the holding time reaches about 7 hours and a gradient in which the hardness increases when the holding time is 7 hours or more are compared. At that time, the latter gradient is very gentler than the former gradient. In the samples in each of which the reduction ratio is 25% or 50%, the hardness increases until the holding time reaches about 7 hours, and the hardness gradually decreases when the holding time exceeds about 7 hours. In the samples in each of which the reduction ratio is 25% or 50%, a gradient in which the hardness increases until the holding time reaches about 7 hours and a gradient in which the hardness decreases when the holding time is 7 hours or more are compared. At that time, the latter gradient (the hardness decreases) is very gentler than the former gradient. In the sample in which the reduction ratio is 25%, the gradient in which the hardness decreases when the holding time is 7 hours or more is steeper than that in the sample in which the reduction ratio is 50%. In the sample in which the reduction ratio is 75%, as the holding time is generally longer, the hardness is higher. In the sample in which the reduction ratio is 75%, a gradient in which the hardness increases until the holding time reaches about 1 hour and a gradient in which the hardness increases when the holding time is 3 hours or more are compared. At that time, the latter gradient is very gentler than the former gradient. In the sample in which the reduction ratio is 75%, a gradient in which the hardness decreases when the holding time is between 1 hour and 3 hours is very gentle.

Next, a case where the samples were subjected to the aging treatment at 500° C. will be described with reference to FIG. 6B. In the sample in which the reduction ratio is 0%, as the holding time is longer, the hardness is higher. In the sample in which the reduction ratio is 0%, a gradient in which the hardness increases until the holding time reaches about 7 hours and a gradient in which the hardness increases when the holding time is 7 hours or more are compared. At that time, the latter gradient is very gentler than the former gradient. In the sample in which the reduction ratio is 25%, the hardness increases until the holding time reaches 3 hours, the hardness very gradually decreases when the holding time is between 3 hours and 7 hours, and the hardness further gradually decreases when the holding time exceeds about 7 hours. In the samples in each of which the reduction ratio is 50% or 75%, the hardness increases until the holding time reaches about 7 hours, and the hardness gradually decreases when the holding time exceeds about 7 hours. In the sample in which the reduction ratio is 50%, the gradient in which the hardness decreases is steeper than that in the sample in which the reduction ratio is 75%.

In all the samples in which the respective reduction ratios are 0%, 25%, 50%, and 75%, a gradient in which the hardness increases in a holding time range of about 0 to 1 hour is larger than a gradient in a holding time range that exceeds 1 hour. Therefore, in a holding time range that exceeds 1 hour, the gradient in which the hardness increases is small. The holding time range that exceeds 1 hour means that the holding time range is any time range including 1 to 3 hours, 3 to 7 hours, 7 to 28 hours, 1 to 7 hours, 1 to 28 hours, 3 to 28 hours, and other time ranges that are exceeds 1 hour. Therefore, when the titanium-tantalum-based alloy containing tin (Sn) is subjected to an aging treatment for at least about 1 hour, proper hardness can be obtained. Accordingly, the holding time in the aging treatment of the titanium-tantalum-based alloy containing tin (Sn) may be 1 hour or less.

In all the samples in which the respective reduction ratios are 0%, 25%, 50%, and 75%, a gradient in which the hardness changes in a holding time range of 7 to 28 hours is gentler than a gradient in a holding time range of 0 to 7 hours. Specifically, in the holding time range of 7 to 28 hours, the hardnesses of the samples reach proper hardness, and do not rapidly change. Therefore, in the holding time range of 7 to 28 hours, the state of each of the samples is regarded as a state where the hardness thereof does not change even after a certain period of time elapses.

Overall, the hardnesses of the samples in which the respective reduction ratios are 25%, 50%, and 75% are larger than the hardness of the sample in which the reduction ratio is 0%. Therefore, it is preferable that the titanium-tantalum-based alloy containing tin (Sn) be subjected to a deformation treatment so that the titanium-tantalum-based alloy containing tin (Sn) harden. Examples of the deformation treatment may includes hot working and cold working or the like.

Next, a case where the samples in each of which the reduction ratio is changed to 0%, 25%, 50%, or 75% by a deformation treatment are subjected to a solution treatment in which the samples are held at 850° C. for 3 hours, followed by an aging treatment at 500° C. will be described with reference to FIG. 6C. In the sample in which the reduction ratio is 0%, as the holding time is longer, the hardness is higher. In the samples in each of which the reduction ratio is 25%, 50%, or 75%, the hardness increases until the holding time reaches about 7 hours, and the hardness very gradually decreases when the holding time exceeds about 7 hours. In the samples in each of which the reduction ratio is 25%, 50%, or 75%, the gradients in which the hardness decreases are almost similar. When the solution treatment and the aging treatment are performed, the hardnesses of the samples reach proper hardness in a holding time range of 7 to 28 hours, and the hardnesses of the samples are regarded as an almost constant state.

Figure 6A:
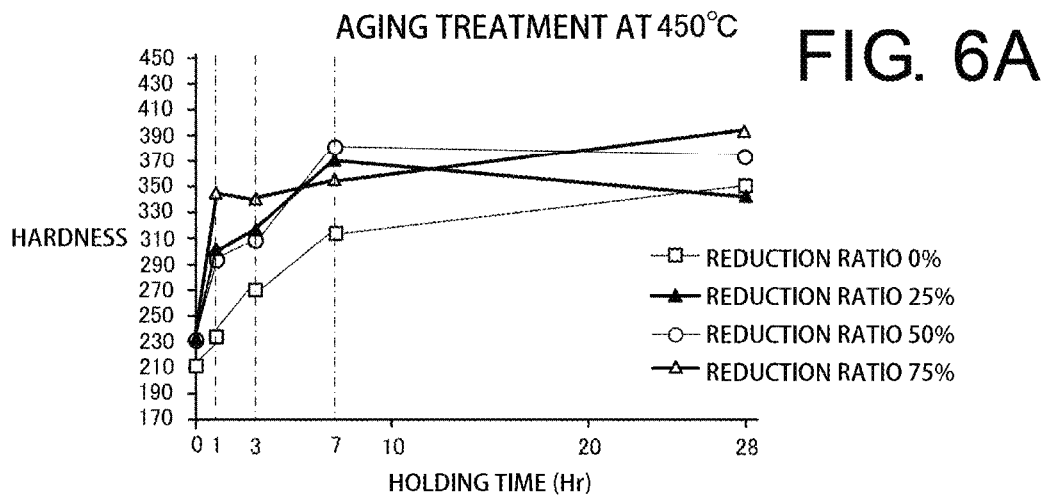
FIGS. 6A, 6B, and 6C are graphs showing a relationship between the holding time and the hardness in an aging treatment of the Ti-23Ta-3Sn alloy in which the reduction ratio is 0%, 25%, 50%, or 75% where
Figure 6B:
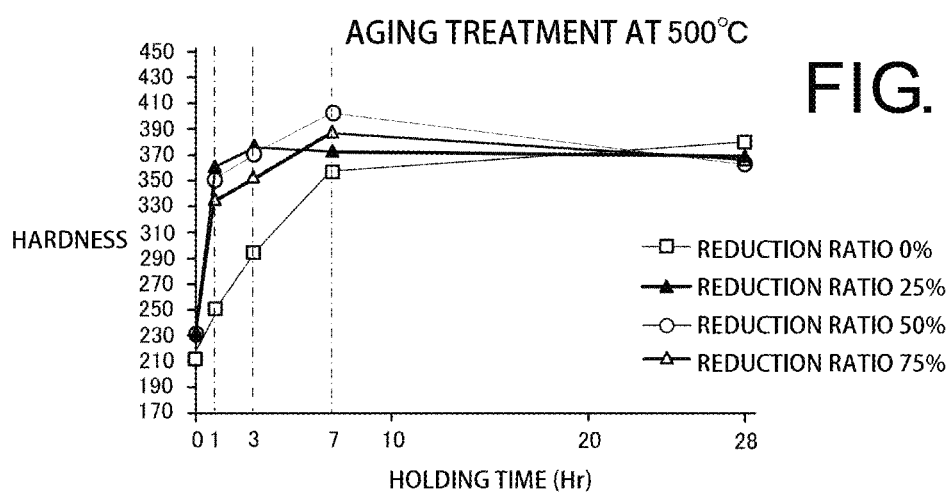
Figure 6C:
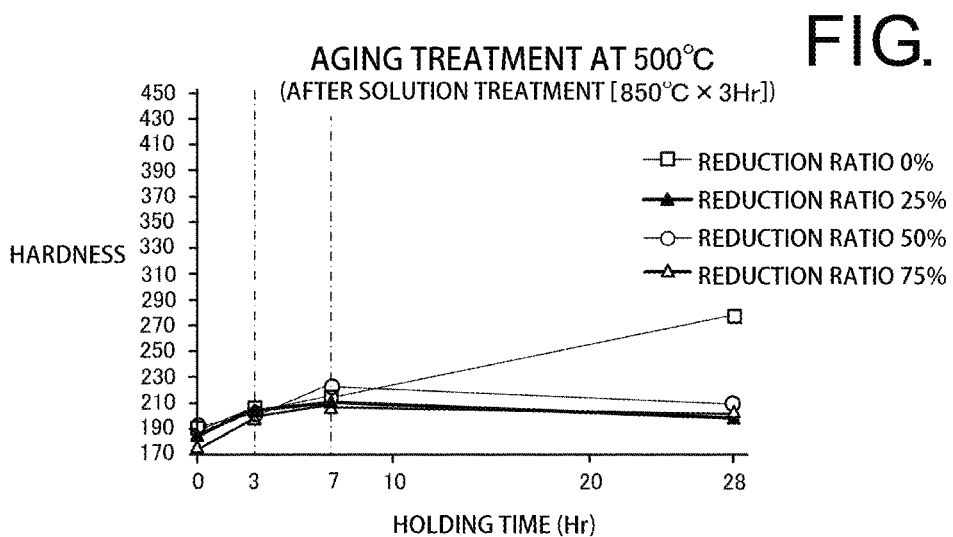

As seen from the results in FIGS. 6A to 6C, the hardnesses of the samples having been subjected the aging treatment at 450° C. or 500° C. increases until the holding time reaches at least about 7 hours regardless of the reduction ratio. When the holding time exceeds about 7 hours, the hardness increases or decreases depending on conditions of the samples. Even when the hardness decreases, the gradient in which the hardness decreases when the holding time exceeds about 7 hours is gentle. Even at a temperature suitable for the aging treatment (aging treatment temperature), it is estimated that the same properties as described above are obtained. For example, the aging treatment temperature may be about 300° C. to about 600° C. The lower limit of the aging treatment temperature is more preferably about 350° C. The upper limit of the aging treatment temperature is more preferably about 550° C.

In the aging treatment of the titanium-tantalum-based alloy containing tin (Sn), the hardness abruptly increases in a holding time range of about 0 to 1 hour regardless of the condition of the sample. The gradient in which the hardness increases in a holding time range of about 1 to 7 hours is gentler than that in the holding time range of about 0 to 1 hour, and the hardness gently decreases when the holding time exceeds 7 hours. Therefore, when the holding time is about 10 hours or less, the hardness close to the maximum value can be imparted to the sample regardless of the condition of the sample. Accordingly, the holding time in the aging treatment of the titanium-tantalum-based alloy containing tin (Sn) at an aging treatment temperature is preferably 10 hours or less, and more preferably 7 hours or less. From the viewpoint of decreasing the time in the production steps, the holding time in the aging treatment of the titanium-tantalum-based alloy containing tin (Sn) may be 1 hour or more and 7 hours or less. When the holding time is 1 hour or less, the hardness abruptly increases. In order to control the hardness within a relatively lower hardness range, the holding time is preferably 1 hour or less.

When the holding time range in the aging treatment of the titanium-tantalum-based alloy containing tin (Sn) is 7 to 28 hours, the range of change in hardness of the alloy is smaller than that in a holding time range of 0 to 7 hours, that is, the hardness of the alloy is not largely changed. Therefore, when the holding time range is 7 to 28 hours, the holding time in the aging treatment may not be precisely controlled in minutes or seconds. When the holding time range in the aging treatment of the titanium-tantalum-based alloy containing tin (Sn) is 7 to 28 hours, the production quality can be stabilized in a simple manner, and the quality control cost can be decreased.

As estimated from FIGS. 6A to 6C, this trend does not change even when the holding time is extended to 30 hours. For this reason, continuity of the treatment over 30 hours or more is not reasonable in terms of production cost. Accordingly, the holding time in the aging treatment of the titanium-tantalum-based alloy containing tin (Sn) at an aging treatment temperature is preferably 7 hours or more and 30 hours or less, and more preferably 7 hours or more and 28 hours or less from the viewpoint of both the production cost and the stability of hardness of the alloy.

1-3-5. Partial Heat Treatment of Material for Angular Plate

The angular plate 1 is formed from the titanium-tantalum-based alloy containing tin (Sn) having the aforementioned properties for a heat treatment such as the solution treatment and the aging treatment. The whole or a part of the material for the angular plate 1 before molding or the whole or a part of the angular plate 1 after molding may be subjected to the heat treatment to increase the hardness of the whole or the part of the angular plate 1. A part in which the hardness of the angular plate 1 is increased is referred to as a hardened part. The hardened part in the angular plate 1 may be provided at any part of the angular plate 1. The number of the hardened part in the angular plate 1 may be one or more.

Figure 7A:
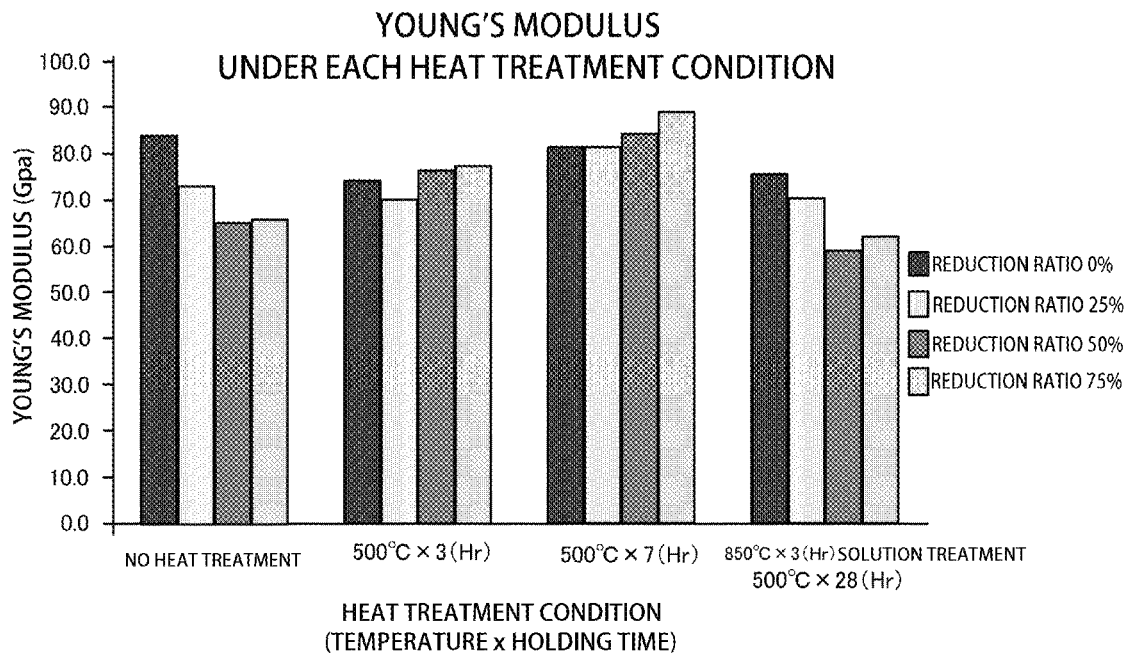
FIG. 7A is a graph showing Young's modulus under each condition of heat treatment of the Ti-23Ta-3Sn alloy in which the reduction ratio is 0%, 25%, 50%, or 75%.

FIG. 7A is a graph showing a relationship between the Young's modulus and the condition of heat treatment of the Ti-23Ta-3Sn alloy. As shown in FIG. 7A, the Young's modulus of the Ti-23Ta-3Sn alloy that has been subjected to the aging treatment at 500° C. for a holding time of 3 hours and the Young's modulus of the Ti-23Ta-3Sn alloy that has been subjected to the aging treatment at 500° C. for a holding time of 7 hours are compared. At that time, the former is smaller than the latter. The Young's modulus of the Ti-23Ta-3Sn alloy that has been subjected to the solution treatment at 850° C. for a holding time of 3 hours followed by the aging treatment at 500° C. for a holding time of 28 hours is smaller than the two Young's moduli described above.

Therefore, when the condition of heat treatment of the Ti-23Ta-3Sn alloy is changed, the Young's modulus of the Ti-23Ta-3Sn alloy can be controlled. In addition to the Ti-23Ta-3Sn alloy, it is estimated that this is similarly applied to the whole titanium-tantalum-based alloys containing tin (Sn). Accordingly, the Young's modulus of each part of the angular plate 1 can be finely controlled by the heat treatment.

In the heat treatment of a part of the material for the angular plate 1 before molding or a part of the angular plate 1 after molding, for example, the part may be irradiated with a laser beam resulting in heating. However, the heat treatment is not limited to this treatment. Examples of the heat treatment may include various treatments including high-frequency induction heating, heating by flame, and heating by irradiation with an electronic beam.

Figure 7B:
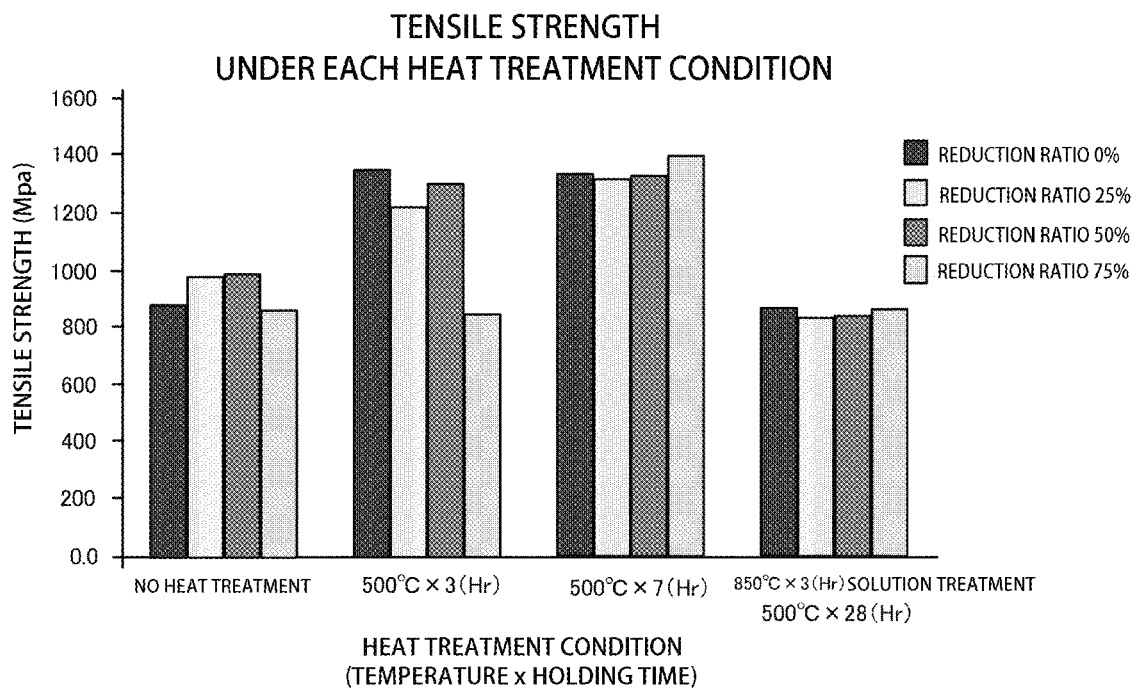
FIG. 7B is a graph showing tensile strength under each condition of heat treatment of the Ti-23Ta-3Sn alloy in which the reduction ratio is 0%, 25%, 50%, or 75%, where the conditions of heat treatment include no heat treatment, holding at 500° C. for 3 hours, holding at 500° C. for 7 hours, and holding at 500° C. for 28 hours after a solution treatment in which holding is performed at 850° C. for 3 hours.

FIG. 7B is a graph showing a relationship between the heat treatment condition and the tensile strength of the Ti-23Ta-3Sn alloy. The tensile strength of the Ti-23Ta-3Sn alloy that has been subjected to the aging treatment at 500° C. for a holding time of 3 hours and the tensile strength of the Ti-23Ta-3Sn alloy that has been subjected to the aging treatment at 500° C. for a holding time of 7 hours are compared. At that time, as shown in FIG. 7B, the tensile strengths of the alloys other than the alloy in which the reduction ratio is 75% are substantially the same, and are high.

Therefore, even when the holding time in the aging treatment of the Ti-23Ta-3Sn alloy is 7 hours or less, it is estimated that the tensile strength does not change and high tensile strength is maintained. In addition to the Ti-23Ta-3Sn alloy, it is estimated that this is similarly applied to the whole titanium-tantalum-based alloys containing tin (Sn).

In consideration of FIGS. 6A to 6C and FIGS. 7A and 7B, when flexibility is required for the titanium-tantalum-based alloy containing tin (Sn) with the hardness increased, it is preferable that the holding time in the aging treatment of the titanium-tantalum-based alloy containing tin (Sn) be about 7 hours or less. When the holding time in the aging treatment of the titanium-tantalum-based alloy containing tin (Sn) is 7 hours or less, high tensile strength is maintained.

1-3-6. Surface Modification of Material for Angular Plate

When the angular plate 1 is formed from the titanium-tantalum-based alloy described above, it is preferable that a surface of the angular plate 1 be subjected to a predetermined treatment. Examples of the predetermined treatment may include a treatment of controlling a surface configuration of the angular plate 1 and a treatment of controlling surface design thereof.

The surface configuration of the angular plate 1 largely affects adhesion, development, arrangement, aggregation, differentiation, and expression configurations of cells. A rough surface generally has a larger adhesive force against cells, as compared with a smooth mirror surface. Therefore, it is preferable that the angular plate 1 be subjected to a treatment of controlling the surface configuration. Examples of the treatment of controlling the surface configuration of the angular plate 1 may include a treatment of roughening the surface of the angular plate 1 by mechanical machining (lath-machined surface), titanium plasma spraying (titanium plasma-sprayed surface), blasting (blasted surface), etching (etched surface), SLA (sand-blasted large-grit acid-etched surface), spherical coating (sintered porous-structured surface), wire electrical discharge machining, anodization, irradiation with a laser beam, or acid etching.

The surface design affects adsorption and adhesion of a material important for a biological reaction with protein, bacteria, and cells, and proliferation and differentiation of cells. Therefore, it is preferable that the angular plate 1 be subjected to a treatment of controlling the surface design. Examples of the treatment of controlling the surface design of the angular plate 1 may include a treatment of forming a coating layer of hydrous titania gel on the surface of the angular plate 1, a surface treatment of coating the surface of the angular plate 1 with a phosphorylated amino acid and/or a phosphorylated peptide, a treatment of imparting an OH group to a coating layer on the surface of the angular plate 1, a treatment of forming a titanium phosphide layer and a calcium phosphate layer on the surface of the angular plate 1, a treatment of coating the surface of the angular plate 1 using plasma, a treatment of coating the surface of the angular plate 1 with calcium phosphate, and a hydrothermal alkaline treatment of the surface of the angular plate 1.

1-3-7. Oxide Film of Material for Angular Plate

When an oxide film is formed on the surface of the titanium-tantalum-based alloy, the oxide film functions as a protective film, and improves corrosion resistance of the titanium-tantalum-based alloy. Therefore, in the angular plate 1 formed from the titanium-tantalum-based alloy having an oxide film, the corrosion resistance of the angular plate 1 is improved. Therefore, when the angular plate 1 is indwelled in the body for an extended period of time, the body is safe. The thickness of the oxide film formed on the surface of the titanium-tantalum-based alloy in the present invention may be controlled in a production stage.

1-3-8. Young's Modulus Gradient Changing Treatment of Material for Angular Plate It is preferable that the angular plate 1 have the elastically deforming part as described above. When the part corresponding to the elastically deforming part of the angular plate 1 is subjected to a treatment of changing the Young's modulus, the degree of elastic deformation in the elastically deforming part can be controlled. As an aspect in which the Young's modulus is changed, various aspects are assumed.

Examples of the aspects may include an aspect in which the Young's modulus continuously gradually decreases (or increases) from the lower portion toward the upper portion of the bone supporting plate part 10 along the longitudinal direction of the bone supporting plate part 10, and an aspect in which the Young's modulus discontinuously changes along the longitudinal direction of the bone supporting plate part 10. However, the present invention is not limited to these aspects, and another aspect may be adopted.

As described above, when the reduction ratio of the titanium-tantalum-based alloy is changed, the Young's modulus also changes. Using the properties of the titanium-tantalum-based alloy, at least a part of the material for the titanium-tantalum-based alloy may be subjected to the deformation treatment so that the reduction ratio of at least the part of the material for the titanium-tantalum-based alloy is changed. Thus, the Young's modulus can be changed.

In the aspect in which the Young's modulus gradient is changed, the deformation treatment for the bone supporting plate part 10 may be performed so that the reduction ratio continuously gradually increases from the lower portion toward the upper portion of the bone supporting plate part 10 along the longitudinal direction of the bone supporting plate part 10. In the aspect in which the Young's modulus gradient is discontinuously changed, the deformation treatment for the bone supporting plate part 10 may be performed so that the reduction ratio discontinuously increases along the longitudinal direction of the bone supporting plate part 10. Specifically, the elastically deforming part may be treated so that the reduction ratio in the angular plate 1 is continuously or discontinuously changed.

As shown in a graph of the reduction ratio of the non-contact part 16 on a right side of FIG. 3, in an aspect in which the Young's modulus gradient of the non-contact part 16 is changed, the reduction ratio continuously increases in a curve shape from a vertex 16a toward a central part 16b of the non-contact part 16, and continuously decreases in a curve shape from the central part 16b toward a bottom 16c.

A method for producing such a non-contact part 16 will be described below with reference to FIGS. 4A to 4D. As shown in FIG. 4A, a force is applied to a surface of a board 700 of the titanium-tantalum-based alloy containing tin (Sn) in a thickness direction of the board 700. As shown in FIG. 4B, a hollow is made on the surface of the board 700. Since the board 700 has a curved hollow on the surface as shown in FIG. 4B, the reduction ratio of the board 700 continuously changes in a curve shape. Specifically, the reduction ratio at a center part of the board 700 is high, and the reduction ratio continuously decreases towards both ends of the board 700.

The deformed surface of the board 700 described above is cut to a predetermined depth (to a dotted line 701 in FIG. 4B) in the thickness direction. Thus, a board 710 having a part in which the reduction ratio continuously changes as shown in FIG. 4C is obtained. The angular plate 1 may be produced so that the part in which the reduction ratio continuously changes corresponds to the non-contact part 16 shown in FIG. 3.

As shown in FIG. 4D, an angular plate 1a having a curved hollow shown in FIG. 4B as the non-contact part 16 may be produced. In this case, the surface of the board 700 is not cut to a predetermined depth in the thickness direction.

As shown in FIG. 5, the titanium-tantalum-based alloy containing tin (Sn) has a property in which the Young's modulus is lower as the reduction ratio is higher. Therefore, when the non-contact part 16 is produced as describe above, the Young's modulus of the non-contact part 16 can be made lower than those of other parts. As shown in FIG. 7A, the titanium-tantalum-based alloy containing tin (Sn) has a property in which the Young's modulus is higher as the holding time in the heat treatment is longer. Therefore, it is preferable that the holding time in the heat treatment of the non-contact part 16 be decreased.

It is preferable that the hardness and strength of parts other than the non-contact part 16 such as a contact part 17, which is a part in contact with the bone part 19a, and the blade part 11 in the bone supporting plate part 10 be higher than those of the non-contact part 16. Therefore, it is preferable that the contact part 17 and the blade part 11 be produced so that the reduction ratio is not high. Further, it is preferable that the holding time in the heat treatment of the contact part 17 and the blade part 11 be increased.

1-3-9. Other Materials Constituting Angular Plate

The angular plate 1 may be formed from the titanium-tantalum-based alloy and a polymer. Examples of an angular plate 1 containing a polymer may include an angular plate in which a part 13a around each of the holes 13 of the angular plate 1 is formed from the polymer and other parts are formed from the titanium-tantalum-based alloy, as shown in FIG. 2B. In another embodiment, the part 13a around each of the holes 13 of the angular plate 1 may be formed from the titanium-tantalum-based alloy and the other parts may be formed from the polymer or the like. Examples of the polymer may include polyetheretherketone (PEEK). However, the polymer is not limited to this, and another polymer may be used.

The angular plate 1 may be formed from the titanium-tantalum-based alloy and a biodegradable material having biocompatibility. As shown in FIG. 2B, in an angular plate 1b formed from titanium-tantalum-based alloy and the biodegradable material, the region near a curve part 10e of the bone supporting plate part 10 is formed from two layers of the titanium-tantalum-based alloy and the biodegradable material in the thickness direction of the bone supporting plate part 10. In this case, one of the two layers is a layer 10c in which the Young's modulus is low (for example, the outer periphery 10b side of the bone supporting plate part 10) and which is formed from the titanium-tantalum-based alloy. Another layer 10d (for example, inner periphery 10a side of the bone supporting plate part 10) is formed from the biodegradable material. Examples of the biodegradable material may include a biodegradable plastic and a biodegradable metal. The biodegradable plastic is hydrolyzed in the living body by an acid or alkali and carried out of the living body. Examples of the biodegradable plastic may include those including polyglycolic acid, polydioxanone, and polylactic acid. Examples of the biodegradable metal may include magnesium (Mg) and a magnesium alloy.

In an initial stage of bone fracture, a bone fracture area is not sufficiently repaired. Therefore, it is preferable that the angular plate 1 to be attached to the bone fracture area have high rigidity. This is because it is preferable that tight fixation of the bone fracture area be preferential when the repair state of the bone fracture area is not sufficient.

After attachment of the angular plate 1 to the bone fracture area, it is preferable that elastic deformation of the angular plate 1 be gradually facilitated as the repair of the bone fracture area proceeds. In order to activate osteoblasts contributing to the repair of the bone fracture area, it is preferable that movement of the bone fracture area to such an extent that excessive stress is not applied to the bone fracture area due to a force to be applied be preferential.

As described above, when a region near the curve part 10e of the bone supporting plate part 10 is formed from the biodegradable plastic or the like into a two-layer structure in the thickness direction of the bone supporting plate part 10, the rigidity of the biodegradable plastic or the like near the curve part 10e is high. This is because hydrolysis of the biodegradable plastic does not advance at the initial state of attaching the angular plate 1 to the bone fracture area. Therefore, the region near the curve part 10e of the bone supporting plate part 10 is reinforced by the biodegradable plastic or the like, and as a result, the rigidity thereof is made high. In contrast, after attachment of the angular plate 1 to the bone fracture area, the hydrolysis of the biodegradable plastic or the like slowly advances. With the time elapsed, the biodegradable plastic or the like gradually disappears from the living body. For this reason, the degree of reinforcement due to the biodegradable plastic or the like gradually decreases. As a result, at the region near the curve part 10e of the bone supporting plate part 10, the elastic deformation is gradually facilitated. The description concerning the biodegradable plastic can be appropriately applied to the biodegradable metal.

2. Second Embodiment 2-1. General Configuration

A plate for an epiphysis 2 that is an implant of a second embodiment of the present invention will be described below with reference to FIGS. 8 and 9. The plate for an epiphysis 2 is mainly used for an epiphysis, and has no blade that is provided to the angular plate 1. The plate for an epiphysis 2 includes a bone supporting plate part 20 and an edge plate part 21.

Figure 8:
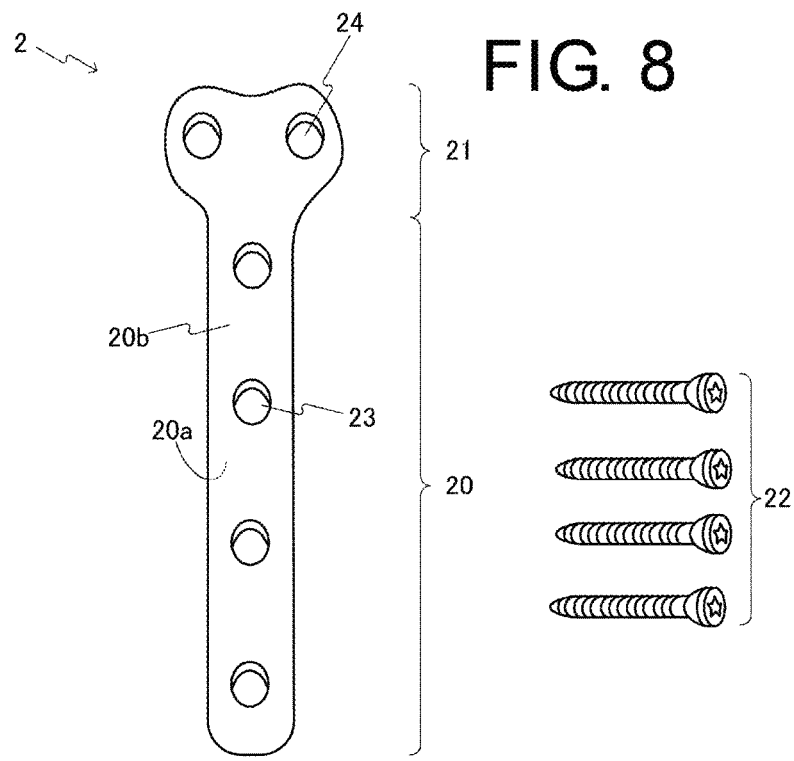
FIG. 8 is a view illustrating a plate for an epiphysis and screw members that are implants in a second embodiment of the present invention.
Figure 9:
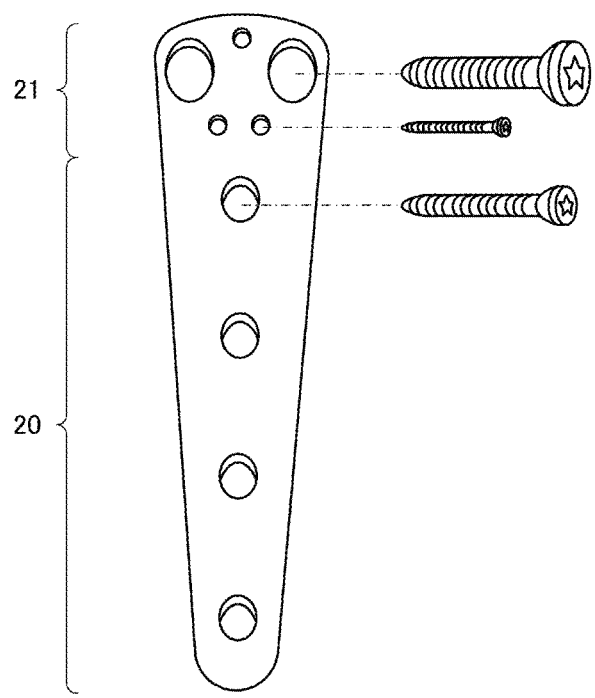
FIG. 9 is a view illustrating a modification of the plate for an epiphysis as the implant in the second embodiment.

As shown in FIG. 8, the bone supporting plate part 20 is formed in a plate shape such as a band. The length of the bone supporting plate part 20 in the widthwise direction is substantially constant over its length. One plane of the bone supporting plate part 20 in the thickness direction (the rear side of the paper of the drawing) is an inner surface 20a of the bone supporting plate part 20. Another plane of the bone supporting plate part 20 in the thickness direction (the top side of the paper) is an outer surface 20b of the bone supporting plate part 20. The inner surface 20a of the bone supporting plate part 20 is a surface to come into contact with the bone, as described below.

As shown in FIG. 8, the edge plate part 21 is formed in a plate shape, and is integrally formed with the bone supporting plate part 20 so as to extend in the longitudinal direction of the bone supporting plate part 20 from one end (upper end) in the longitudinal direction of the bone supporting plate part 20. The edge plate part 21 has such a structure that the width thereof spreads outside the bone supporting plate part 20 in the widthwise direction. Specifically, the width of the edge plate part 21 is larger than the width of the bone supporting plate part 20.

The plate for an epiphysis 2 has a plurality of holes 23 and 24. The holes 23 are each a hole through which a screw member 22 is allowed to pass. The holes 23 are arranged in a line at certain intervals in the longitudinal direction of the bone supporting plate part 20. At least two holes 24 are provided in the edge plate part 21, and are arranged in a line in the widthwise direction of the bone supporting plate part 20. The screw members 22 and the holes 23 and 24 are substantially the same as the screw members 12 and the holes 13, which are described with reference to FIG. 1A. Therefore, the description for the screw member 22 and the holes 23 and 24 is omitted.

The width of the bone supporting plate part 20 is substantially constant over the whole length in the longitudinal direction as shown in FIG. 8, but the bone supporting plate part 20 is not limited thereto. As shown in FIG. 9, the bone supporting plate part 20 may be in a taper shape in which the length of the bone supporting plate part 20 in the widthwise direction is decreased in a direction from the boundary between the bone supporting plate part 20 and the edge plate part 21 (one end (upper end) of the bone supporting plate part 20) toward another end (lower end).

Holes are provided in the bone supporting plate part 20 and the edge plate part 21. The holes may have various diameters, for example, as shown in FIG. 9. Screw members corresponding to the diameters of the holes as shown in FIG. 9 are used.

From the same reason as described in the angular plate 1, it is preferable that the plate for an epiphysis 2 at least partially have an elastically deforming part that is elastically deformable. Examples of apart corresponding to the elastically deforming part may include the whole plate for an epiphysis 2, the bone supporting plate part 20, the edge plate part 21, a junction between the bone supporting plate part 20 and the edge plate part 21, a part thereof, and a combination thereof. The elastically deforming part may be formed from an elastically deformable material.

It is preferable that at least a part of the plate for an epiphysis 2 be formed from a material having moderately low elastic limit. When the part of the plate for an epiphysis 2 is formed from a material having moderately low elastic limit, the part of the plate for an epiphysis 2 can be plastically deformed with ease.

2-2. Attachment of Plate for Epiphysis to Bone Fracture Area

Figure 10:
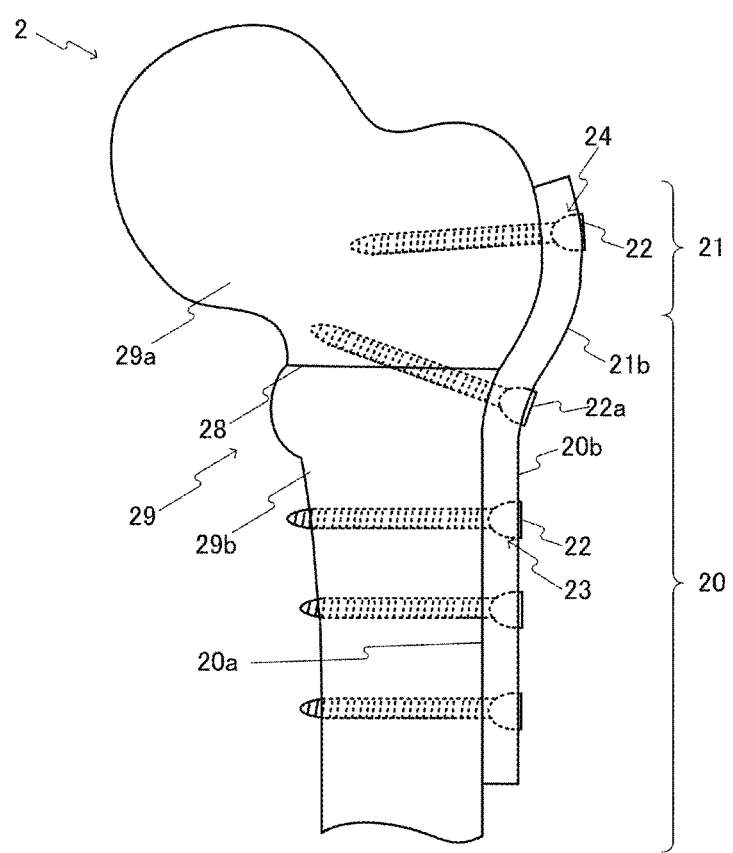
FIG. 10 is a view illustrating a state where the plate for an epiphysis as the implant in the second embodiment is attached to a bone fracture area.

Next, when a bone 29 is fractured into a bone part 29a in the vicinity of the distal and a bone part 29b on a side of a main body, a procedure of attaching the plate for an epiphysis 2 to a bone fracture area will be described with reference to FIG. 10. In attachment of the plate for an epiphysis 2 to the bone fracture area, the bone supporting plate part 20 is disposed over a bone fracture part 28 that represents a surface of fractured part of the bone 29 so that an inner surface 20a of the bone supporting plate part 20 comes into contact with an outer periphery of the bone part 29b, as shown in FIG. 10. The bone supporting plate part 20 is deformed into a shape corresponding to the shape of the outer periphery of the bone part 29b so that the inner surface 20a of the bone supporting plate part 20a comes into contact with the outer periphery of the bone part 29b. In this case, a force exceeding the elastic limit is applied to the bone supporting plate part 20.

The edge plate part 21 is brought into contact with the outer periphery of the bone part 29a that is one part of the bone separated at the bone fracture part 28. Similarly to the bone supporting plate part 20, the edge plate part 21 may be formed into a shape corresponding to the shape of the outer periphery of the bone part 29a.

Each of the screw members 22 is then threaded into the bone part 29b through each of the holes 23 from an outer surface 20b side of the bone supporting plate part 20, and threadedly engaged with the bone part 29b. Like a screw member 22a, the screw members 22 may be threadedly engaged over the bone parts 29b and 29a. Each of the screw members 22 is threaded into the bone part 29a through each of the holes 24 from an outer surface 21b side of the edge plate part 21, and threadedly engaged with the bone part 29a in the same manner as described above. When the screw members 22 are threadedly engaged into the bone parts 29a and 29b, the bone supporting plate part 20 and the edge plate part 21 are elastically deformed to come into tight contact with the outer periphery of the bone 29. Specifically, the plate for an epiphysis 2 is disposed over the bone fracture part 28 and fixes the bone fracture area of the bone 29 so as to come into contact with the outer periphery of the bone 29. As described above, the plate for an epiphysis 2 is used to achieve connection in the bone fracture area of the bone 29.

2-3. Material for Plate for Epiphysis

A material for the plate for an epiphysis 2 is the same as the material for the angular plate 1 described in <1-3. Material for Angular Plate>. The description of <1-3. Material for Angular Plate> can also be applied to the plate for an epiphysis 2.

3. Third Embodiment 3-1. General Configuration

Figure 11:
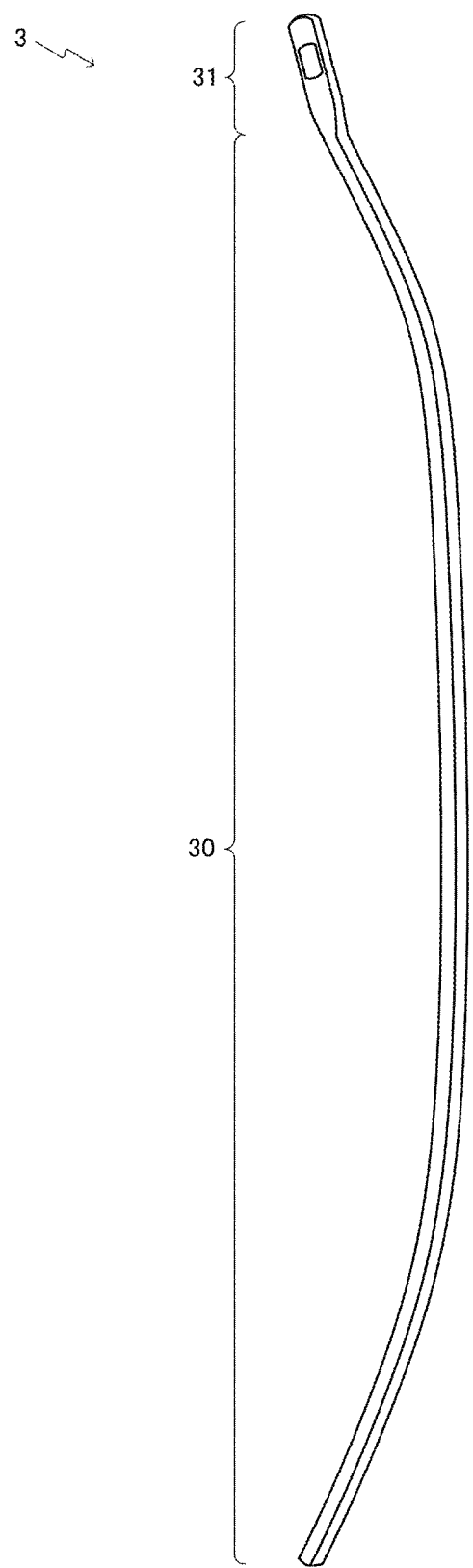
FIG. 11 is a view illustrating an intramedullary nail that is an implant in a third embodiment of the present invention.
Figure 12:
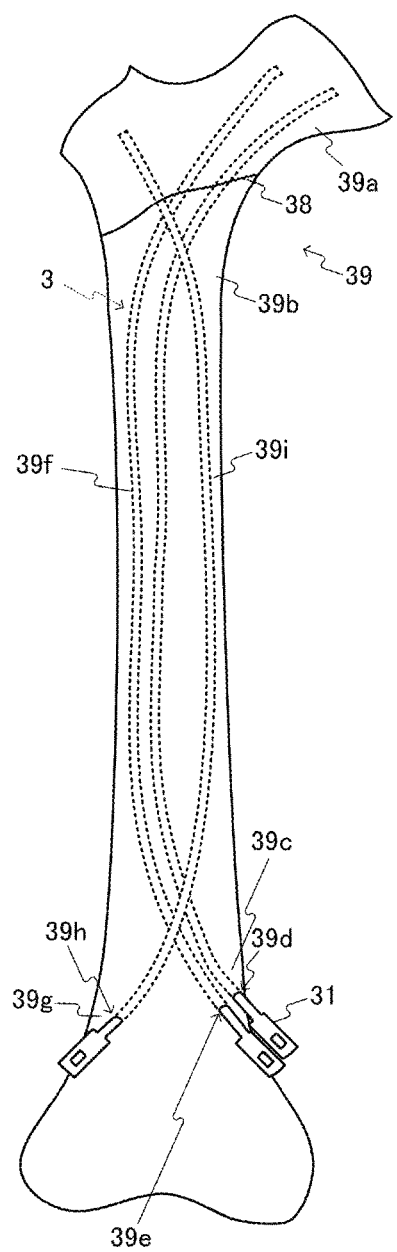
FIG. 12 is a view illustrating a state where the intramedullary nail as the implant in the third embodiment is attached to a bone fracture area.

An intramedullary nail 3 that is an implant of a third embodiment of the present invention will be described below with reference to FIGS. 11 and 12. The intramedullary nail 3 is referred to as an ender nail. As shown in FIG. 11, the intramedullary nail 3 has a linear structure part 30 and a head part 31.

The linear structure part 30 is formed in a linear shape or a bar shape. For example, the shape of cross section of the linear structure part 30 may be a curved shape such as a circular shape or an elliptical shape or a polygon such as a tetragon or a pentagon, though the shape thereof is not particularly limited. As shown in FIG. 11, the linear structure part 30 is in an arched shape. However, the shape of the linear structure part 30 may be a shape in which the linear structure part 30 can be curved or bent into another shape using a predetermined device.

The head part 31 is a part that is one end of the linear structure part 30 and is formed in a plate shape. The head part 31 has a structure which spreads outward in the widthwise direction of the linear structure part 30 beyond both ends in the widthwise direction of the linear structure part 30. Specifically, the width of the head part 31 is larger than the width of the linear structure part 30.

From the same reason as described in the angular plate 1, it is preferable that the intramedullary nail 3 at least partially have an elastically deforming part that is elastically deformable. Examples of apart corresponding to the elastically deforming part may include the whole intramedullary nail 3, the linear structure part 30, the head part 31, a junction between the linear structure part 30 and the head part 31, a part thereof, and a combination thereof. The elastically deforming part may be formed from an elastically deformable material.

It is preferable that at least a part of the intramedullary nail 3 be formed from a material having moderately low elastic limit. When at least a part of the intramedullary nail 3 is formed from a material having moderately low elastic limit, the part of the intramedullary nail 3 can be plastically deformed with ease. Therefore, the intramedullary nail 3 can be deformed according to the shape or diameter of a bone of a patient.

3-2. Attachment of Intramedullary Nail to Bone Fracture Area

Hereinafter, when a bone 39 is fractured into a bone part 39a in the vicinity of the distal and a bone part 39b on a side of a main body, a procedure of attaching the intramedullary nail 3 to a bone fracture area will be described with reference to FIG. 12. In attachment of the intramedullary nail 3 to the bone fracture area, the linear structure part 30 is placed into the bone parts 39a and 39b, into which the bone is divided, over a bone fracture part 38 that represents a surface of fractured part of the bone 39. The head part 31 is disposed below the bone part 39b (on the distal side with respect to the bone part 39a).

When three intramedullary nails 3 are inserted into the bone 39, for example, two of the intramedullary nails 3 are inserted into the bone in parallel, and the rest is inserted into the bone 39 so as to intersect the two intramedullary nails 3 at any position. Specifically, the two intramedullary nails 3 are inserted into the bone 39 from holes 39d and 39e that are formed on a side face 39c on the distal side of the bone part 39b on the basis of the bone part 39a in the longitudinal direction, and come into contact with an inside surface 39f of the bone part 39b in the longitudinal direction at any position. The end of each of the intramedullary nails 3 enters the bone part 39a so that the intramedullary nails 3 are bent. The rest of the intramedullary nails 3 is inserted into the bone 39 from a hole 39h formed on another side face 39g on the distal side of the bone part 39b on the basis of the bone part 39a in the longitudinal direction, and come into contact with an inside surface 39i of the bone part 39b in the longitudinal direction at any position. The end of the intramedullary nail 3 enters the bone part 39a so that the intramedullary nail 3 is bent. Therefore, the bone part 39a is held by the three intramedullary nails 3 of which the insertion directions are different. Thus, the posture of the bone part 39a is stabilized. As described above, the three intramedullary nails penetrate the inside of the bone part 39b over the bone fracture part 38 and fix the bone part 39a on the bone part 39b.

3-3. Material for Intramedullary Nail

A material for the intramedullary nail 3 is the same as the material for the angular plate 1 described in <1-3. Material for Angular Plate>. The description of <1-3. Material for Angular Plate> can also be applied to the intramedullary nail 3.

4. Fourth Embodiment 4-1. General Configuration

Figure 13:
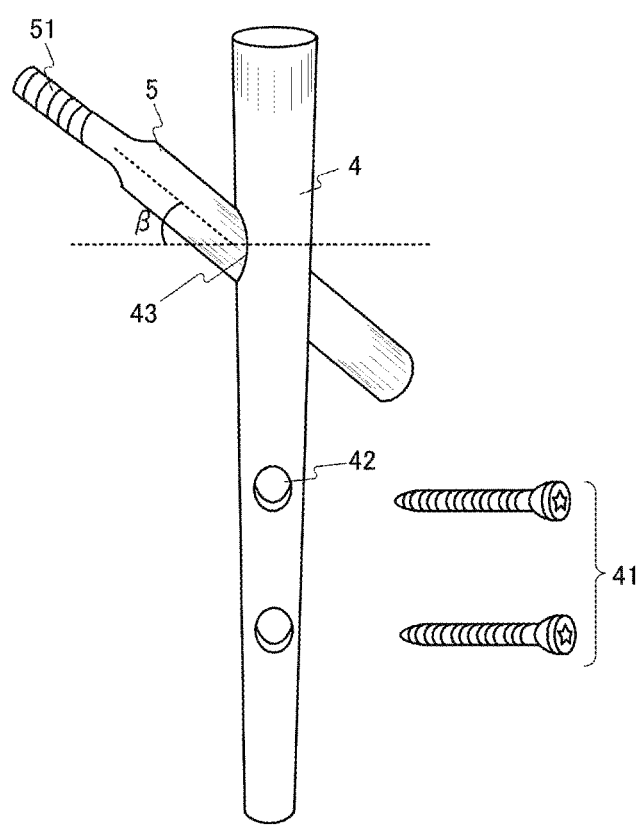
FIG. 13 is a view illustrating a nail and a lag-screw that are implants in a fourth embodiment of the present invention.
Figure 14:
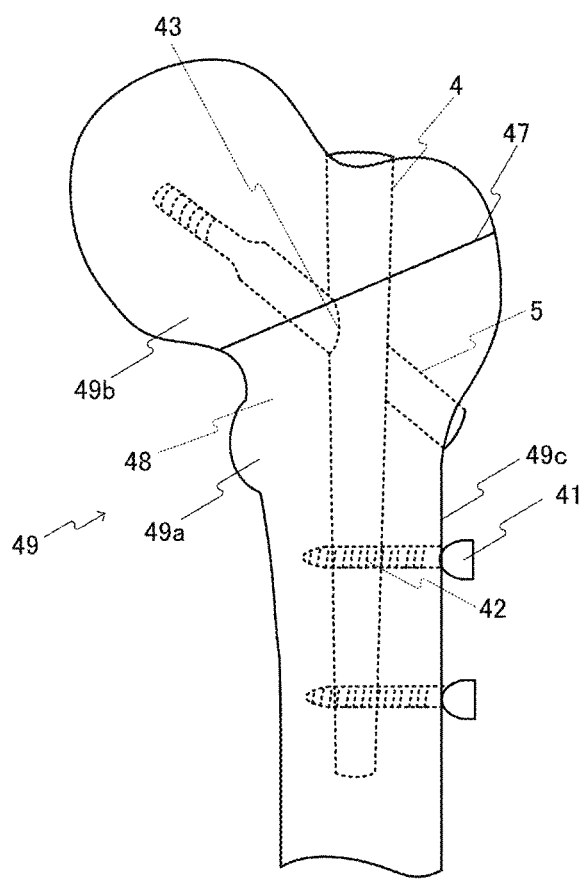
FIG. 14 is a view illustrating a state where the nail and the lag-screws as the implants in the fourth embodiment are attached to a bone fracture area.

A nail 4 and a lag-screw 5 that are implants of a fourth embodiment of the present invention will be described below with reference to FIGS. 13 and 14. For example, the nail 4 is configured to be inserted into the marrow cavity from the proximal end side of the femur and is a substantially columnar member. Examples of the nail 4 may include a substantially columnar member that is formed into a taper shape so as to be easily inserted into the marrow cavity, as shown in FIG. 13, though the nail 4 is not particularly limited to this member. The shape of the nail 4 may be another shape.

In the nail 4, for example, a plurality of holes 42 that penetrate the nail 4 in a radial direction (thickness direction) of the nail 4 are provided. Each of screw members 41 is allowed to pass through each of the holes 42. The holes 42 are arranged in a line at predetermined intervals in the longitudinal direction of the nail 4. A penetrating hole 43 that slantingly penetrates the nail 4 at a predetermined angle β (0<β<90°) relative to the radial direction (thickness direction) of the nail 4 is provided at the upper part in the longitudinal direction of the nail 4.

The lag-screw 5 includes a substantially columnar member. On the end of the substantially columnar member constituting the lag-screw 5, a screw groove 51 is formed. As shown in FIG. 13, the lag-screw 5 is allowed to pass through the penetrating hole 43 of the nail 4. When the lag-screw 5 is allowed to pass through the penetrating hole 43, the lag-screw 5 penetrates the nail 4 at a predetermined angle β (0<β<90°) relative to the radial direction of the nail 4.

Therefore, it is preferable that the nail 4 and the lag-screw 5 at least partially have an elastically deforming part that is elastically deformable. Examples of a part corresponding to the elastically deforming part may include the nail 4, the lag-screw 5, apart thereof, and a combination thereof. The elastically deforming part may be formed from an elastically deformable material.

It is preferable that at least a part of the nail 4 and the lag-screw 5 be formed from a material having moderately low elastic limit. When the part of the nail 4 and the lag-screw 5 is formed from a material having moderately low elastic limit, at least the part of the nail 4 and the lag-screw 5, for example, the nail 4, can be plastically deformed with ease.

4-2. Attachment of Nail and Lag-Screw to Bone Fracture Area

Next, a procedure of attaching the nail 4 and the lag-screw 5 to a bone fracture area will be described with reference to FIG. 14. For example, a case of using the nail 4 and the lag-screw 5 in bone fracture between a femoral body 49a and a caput 49b of a femur 49 as shown in FIG. 14 will be described. First, the nail 4 is inserted into a marrow cavity 48 from the proximal end side of the femur 49.

The lag-screw 5 is threaded into the femur 49 in a direction from the femoral body 49a toward the caput 49b across a bone fracture part 47 so as to pass through the penetrating hole 43, and threadedly engaged with the femur 49. Thus, the lag-screw 5 pulls the caput 49b toward the femoral body 49a side, and as a result, the femoral body 49a and the caput 49b are connected.

Each of the screw members 41 is then threaded into the femur 49 in a direction from an outer periphery 49c side of the femoral body 49a toward the holes 42 of the nail 4, and threadedly engaged with the femur 49. As a result, the posture of the nail 4 at the upper portion is fixed in the femur 49 by the lag-screw 5 and the posture of the nail 4 at the lower position is fixed in the femur 49 by the screw members 41. As described above, the nail 4 and the lag-screw 5 are used to achieve connection in the bone fracture area of the femur 49.

4-3. Material for Nail and Lag-Screw

A material for the nail 4 and the lag-screw 5 is the same as the material for the angular plate 1 described in <1-3. Material for Angular Plate>. The description of <1-3. Material for Angular Plate> can also be applied to the nail 4 and the lag-screw 5.

5. Fifth Embodiment 5-1. General Configuration

Figure 15:
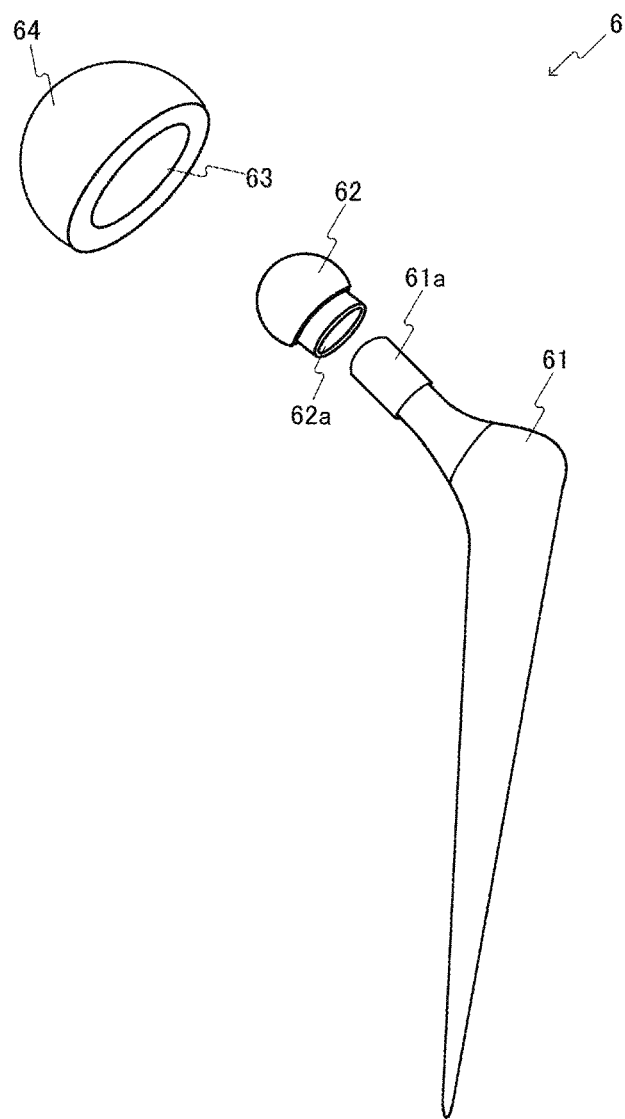
FIG. 15 is a view illustrating an artificial hip joint that is an implant in a fifth embodiment of the present invention.

An artificial hip joint 6 that is an implant of a fifth embodiment of the present invention will be described below with reference to FIG. 15. The artificial hip joint 6 includes a stem 61, a bone head ball 62, a liner 63, and a socket 64. For example, the stem 61 is inserted into the femur for fixation. In order to improve the fixation to a bone such as the femur, for example a surface of the stem 61 is coated with hydroxyapatite.

The bone head ball 62 is a ball-shaped member having an engagement hole 62a that is engaged with a taper part 61a. When the taper part 61a that is an end of the stem 61 is inserted into the engagement hole 62a of the bone head ball 62, the bone head ball 62 is held by the stem 61.

The liner 63 and the socket 64 form a hemi-spherical part, and the liner 63 is disposed inside an inner side of the socket 64. The bone head ball 62 is attached to the liner 63 so as to be rocked on the inner surface of the liner 63.

5-2. Material for Artificial Hip Joint

A material for the artificial hip joint 6 is the same as the material for the angular plate 1 described in <1-3. Material for Angular Plate>. The description of <1-3. Material for Angular Plate> can also be applied to the artificial hip joint 6.

The stem 61, the bone head ball 62, and the socket 64 in the artificial hip joint 6 may be formed from the same material as the material for the angular plate 1 described in <1-3. Material for Angular Plate>, and the liner 63 may be formed from a polymer such as polyethylene or polyether ether ketone. The liner 63 may be surface-treated with an MPC polymer. The MPC polymer represents a polymer of 2-methacryloyloxyethylphosphorylcholine (MPC) having a phospholipid polar group (phosphorylcholine group) and a methacryloyl group in the molecule. For example, the liner

63 may be formed from 64 titanium (for example, Ti-6Al-4V) or a Co—Cr—Mo alloy. In this case, the abrasion between the bone head ball 62 and the liner 63 can be decreased.

6. Other Embodiments

Examples of the implants in other embodiments may include a plate for a clavicle used in bone fracture of a clavicle and a plate for a calcaneus used in bone fracture of a calcaneus. However, the implants are not limited thereto. In addition, the present invention encompasses all implants used in osteopathy.

The implant of the present invention is not limited to the implants used in osteopathy. For example, the present invention also encompasses all implants used in each part of the living body, including an implant used in surgeries on various living bodies such as a bar to be placed subcutaneously in a surgery for pectus excavatum through a submuscular Nuss procedure.

For example, the implant of the present invention may be a head holding member of slidably, smoothly, or freely holding each head of two screw members that are threaded into the bone fracture area or the like in a v shape. In the head holding member, the movement of one screw member is restricted by the movement of the other screw member. Thus, the two threaded screw members can be prevented from being detached from the bone fracture area.

It is preferable that the implants described above also at least partially have an elastically deforming part that is elastically deformable. It is preferable that at least a part of each of the aforementioned implants be formed from a material having moderately low elastic limit. When the part of each of the aforementioned implants is formed from a material having moderately low elastic limit, the part of each of the implants can be plastically deformed with ease.

Materials for the aforementioned implants are the same as the material for the angular plate 1 described in <1-3. Material for Angular Plate>. The description of <1-3. Material for Angular Plate> can also be applied to the aforementioned implants.

7. Production Method

One example of a method for producing an implant in an embodiment of the present invention will be described below with reference to FIG. 16.

First, one ingot of the titanium-tantalum-based alloy containing tin (Sn) is subjected to a deformation treatment (hereinafter referred to as first deformation treatment) (Step S100). As a result, the reduction ratio of the ingot is changed. Examples of the first deformation treatment may include hot working. However, the first deformation treatment is not limited thereto, and may be a treatment concerning another deformation. The hot working represents plastic working in which a metal is heated at a temperature equal to or higher than the recrystallization temperature. Examples of the plastic working may include rolling, stretching, and wire drawing. However, the plastic working is not limited thereto, and may be another plastic working.

An intermediate of an implant formed by the first deformation treatment of the ingot is subjected to a deformation treatment that is different from the first deformation treatment (hereinafter referred to as a second deformation treatment) (Step S101). The second deformation treatment corresponds to a molding treatment. By the second deformation treatment, the appearance shape of the implant is formed, and the reduction ratio of the intermediate is changed. Examples of the second deformation treatment may include cold working (such as bending, drawing, pressing, forging, rolling, extruding, and wire drawing) and cutting. However, the second deformation treatment is not limited thereto, and may be a deformation treatment concerning another molding. The cold working represents working at normal temperature or a temperature lower than the recrystallization temperature of a material. Examples of the cold working may include bending, drawing, cutting, pressing, rolling, forging, extruding, and wire drawing. However, the cold working is not limited thereto, and may be another working.

The whole or a part of the ingot may be subjected to the first deformation treatment. The whole or a part of the intermediate of the implant may be subjected to the second deformation treatment. As one aspect, in the first and second deformation treatments, a part of the ingot or a part of the intermediate may be deformed until the reduction ratio reaches a predetermined value, and at least a part of the rest of the ingot or at least a part of the rest of the intermediate may be deformed until the reduction ratio reaches a value different from the predetermined value (high or low reduction ratio).

When the reduction ratio of the ingot is increased in the first and second deformation treatments, the Young's modulus of the ingot can be decreased as described with reference to FIG. 5. Therefore, in any case, the Young's modulus of a part where the reduction ratio of the ingot is increased is decreased. In the ingot, the part where the reduction ratio is increased may be appropriately used for an elastically deforming part in the implant.

Subsequently, the intermediate of the implant having been subjected to the second deformation treatment is subjected to a heat treatment, if necessary (Step S102). The whole intermediate of the implant having been subjected to the second deformation treatment may be subjected to the heat treatment. Alternatively, only a desired part of the intermediate having been subjected to the second deformation treatment may be subjected to the heat treatment, to form apart (hardened part) where the hardness is made higher than those of other parts in the intermediate. The heat treatment in Step S102 may be performed before or after the first deformation treatment in Step S100. Any of the ingot before Step S100 and the intermediate of the implant after Step S100 may be subjected to the heat treatment in Step S102.

Examples of the heat treatment may include a solution treatment and an aging treatment. The solution treatment is a heat treatment in which a material is heated, and a deposit is dissolved in a solid solution to obtain a single-phase structure of β phase. When an α+β alloy is subjected to the solution treatment, a β phase structure can be obtained while an α phase is left. The aging treatment is a heat treatment in which a deposit (α phase) is deposited in a β phase by heating. The solution treatment and the aging treatment are separate treatments, and may be separately performed in any timing from before Step S100 to after Step S101. The aforementioned procedure is encompassed by the present invention.

Next, the intermediate of the implant after the aforementioned steps is subjected to final machining (Step S103). As a result, the implant is completed. Examples of the final machining may include abrading a surface of the intermediate of the implant, removing a burr formed in the intermediate of the implant, and forming a hole through which a screw member is allowed to pass. However, the final machining is not limited thereto, and all other final machining processes for products are encompassed by the present invention.

In the production steps described above, one ingot is subjected to the first and second deformation treatments so that the reduction ratios of parts constituting the ingot are different. In this case, parts having different Young's moduli are mixed in the ingot. Therefore, an implant having parts in which the degrees of elastic deformation are varied can be produced. For example, it is preferable that a part in which elastic deformation is caused most easily among the parts constituting the implant be a part in which the reduction ratio is made higher in the whole implant. Accordingly, when the reduction ratio of the ingot or the intermediate of the implant is controlled, an ideal implant having parts in which the rigidity and the Young's modulus are varied can be produced.

In any stage of the production steps described above, an oxide film may be formed on the ingot or the intermediate of the implant (oxide film forming step). When the oxide film is formed, the oxide film functions as a protective film, and improves the corrosion resistance of the implant.

One example of a method for producing an implant in another embodiment of the present invention will be described below with reference to FIG. 17. The method for producing an implant in this embodiment is based on the following point. A first part of an implant is formed from a first ingot, a second part of the implant is formed from a second ingot, and the implant is completed by combination of the first part with the second part.

First, a first ingot of the titanium-tantalum-based alloy containing tin (Sn) is subjected to a first deformation treatment (hereinafter referred to as first ingot first deformation treatment) (Step S110). A second ingot of the titanium-tantalum-based alloy containing tin (Sn) is subjected to the first deformation treatment (hereinafter referred to as second ingot first deformation treatment) (Step S111).

Subsequently, a first intermediate of the implant that is formed by the first deformation treatment of the first ingot is subjected to a second deformation treatment (hereinafter referred to as first intermediate second deformation treatment) (Step S112). A second intermediate of the implant that is formed by the first deformation treatment of the second ingot is subjected to the second deformation treatment (hereinafter referred to as second intermediate second deformation treatment) (Step S113). The second deformation treatment corresponds to a molding treatment, as described above. By the second deformation treatment, the appearance shapes of the first and second parts of the implant are formed.

The whole or a part of the first ingot may be subjected to the first ingot first deformation treatment. In one aspect of the first ingot first deformation treatment, a part of the first ingot may be deformed so as to exhibit a predetermined reduction ratio, and at least a part of the rest of the first ingot may be deformed so as to exhibit a reduction ratio different from the predetermined reduction ratio (high or low reduction ratio). Similarly, the whole or a part of the second ingot may be subjected to the second ingot first deformation treatment. In one aspect of the second ingot first deformation treatment, a part of the second ingot may be deformed so as to exhibit a predetermined reduction ratio, and at least apart of the rest of the second ingot may be deformed so as to exhibit a reduction ratio different from the predetermined reduction ratio (high or low reduction ratio). The whole or a part of the first intermediate may be subjected to the first intermediate second deformation treatment. In one aspect of the first intermediate second deformation treatment, a part of the first intermediate may be deformed so as to exhibit a predetermined reduction ratio, and at least a part of the rest of the first intermediate may be deformed so as to exhibit a reduction ratio different from the predetermined reduction ratio (high or low reduction ratio). The whole or a part of the second intermediate may be subjected to the second intermediate second deformation treatment. In the second intermediate second deformation treatment, a part of the second intermediate may be deformed so as to exhibit a predetermined reduction ratio, and at least a part of the rest of the second intermediate may be deformed so as to exhibit a reduction ratio different from the predetermined reduction ratio (high or low reduction ratio).

In any case, the Young's modulus of a part where the reduction ratio is increased is lower than that before increasing the reduction ratio. As described above, the implant of the present invention may partially include an elastically deforming part. Any part of the first or second intermediate in which the reduction ratio is increased may be appropriately used as the elastically deforming part of the implant. The reduction ratio of the elastically deforming part of the implant may be varied depending on the degree of elastic deformation required for the implant.

Subsequently, the first or second intermediate of the implant may be subjected to a heat treatment, if necessary (Step S114). The heat treatment is the same as the heat treatment described in the embodiment with reference to FIG. 16, and is already described. Therefore, the description of the heat treatment is omitted. The whole or a part of the first intermediate or the whole or a part of the second intermediate of the implant may be subjected to the heat treatment. Thus, a hardened part in which the hardness is made higher than those of other parts in the first or second intermediate may be provided.

Timing of the heat treatment is not particularly limited to immediately after Steps S112 and S113. The heat treatment may be performed before or after any step. Specifically, the heat treatment may be performed before Steps S112 and S113, or after the final machining step of S115.

The first or second intermediate of the implant after the aforementioned steps is subjected to final machining (Step S115). As a result, the first or second part of the implant is completed. The final machining is the same as the final machining described in the embodiment with reference to FIG. 16, and is already described. Therefore, the description of the final machining is omitted. The first and second parts of the implant are assembled (Step S116), to complete the implant.

In any stage of the production steps described above, an oxide film may be formed on a surface of the first or second ingot or the first or second intermediate (oxide film forming step). When the oxide film is formed, the oxide film functions as a protective film, and finally improves the corrosion resistance of the implant.

Methods for producing an implant including steps for each treatment described above that are appropriately selected and combined are all encompassed by the present invention.

In the production steps described above, it is preferable that a part in which elastic deformation is caused most easily among the parts constituting the implant be a part in which the reduction ratio is higher in the first or second intermediate of the implant. Accordingly, when the reduction ratio of the first or second intermediate of the implant is controlled, an ideal implant having parts in which the rigidity and the Young's modulus are varied can be produced.

Figure 16:
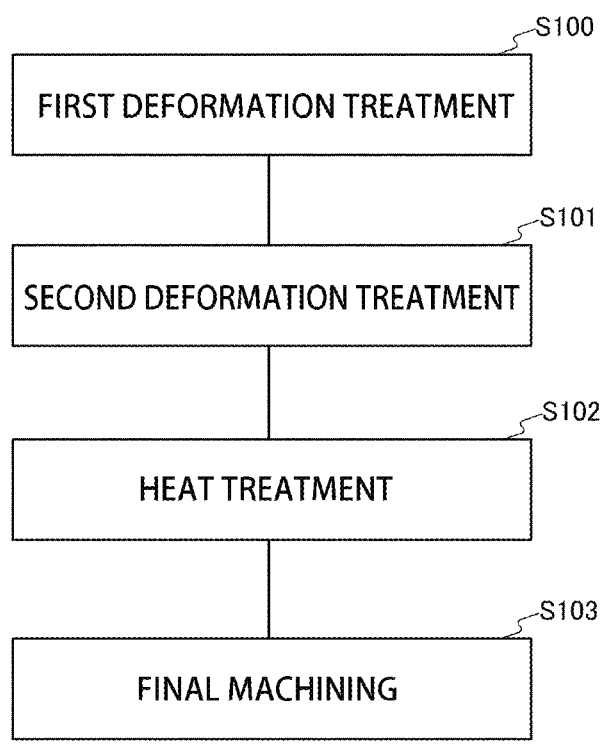
FIG. 16 is a flow chart showing a method for producing an implant in an embodiment of the present invention.
Figure 17:
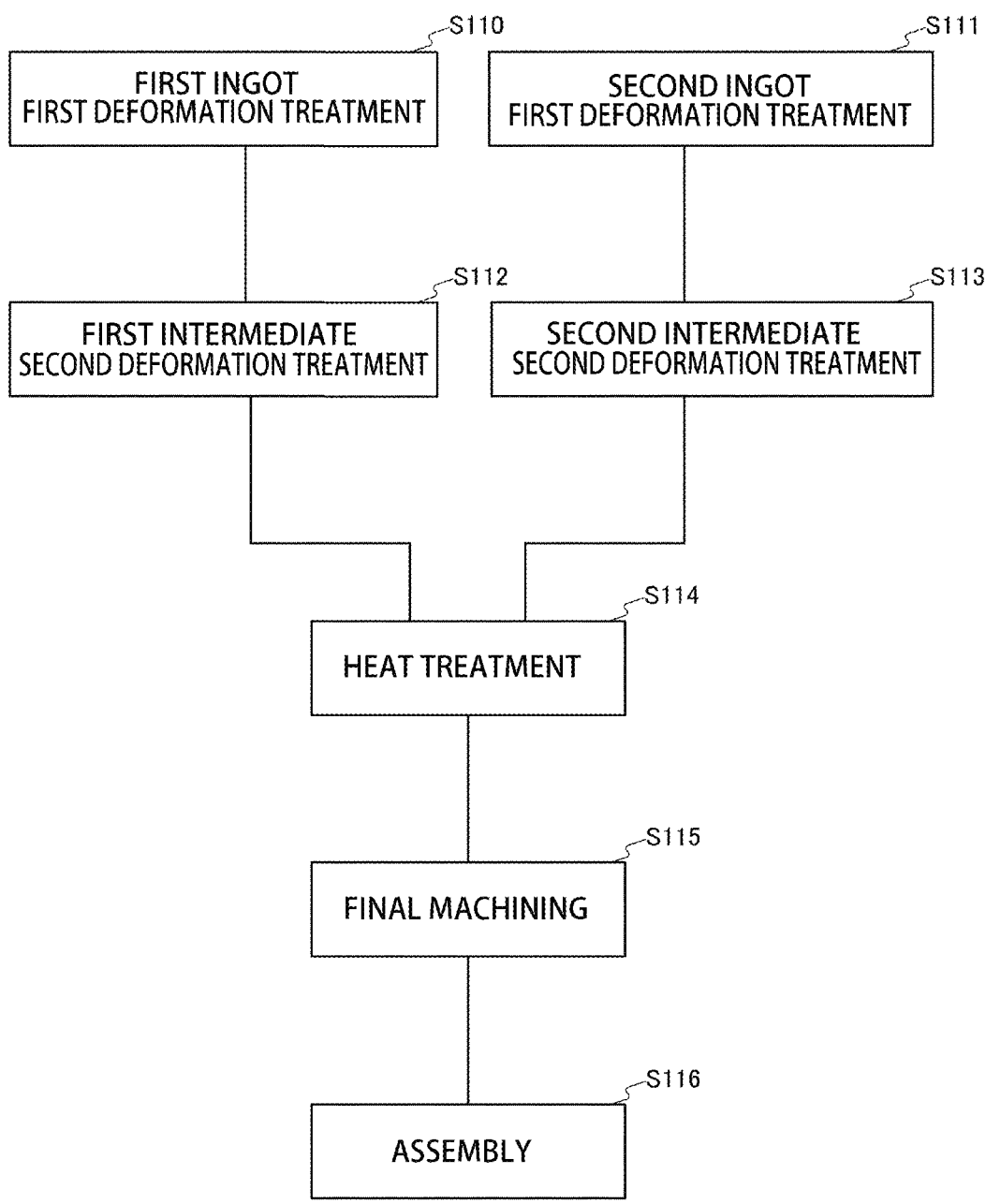
FIG. 17 is a flow chart showing a method for producing an implant in another embodiment of the present invention.

In the methods for producing an implant shown in FIGS. 16 and 17, an ingot is subjected to the first and second deformation treatments and the heat treatment to control the Young's modulus. A specific aspect of controlling the Young's modulus will be described below.

For example, when the bone supporting plate part 10 and the blade part 11 are formed by bending (second deformation treatment) in the production of the angular plate 1 shown in FIGS. 1A, 1B, and 1C, the Young's modulus of a part that is bent (second deformation treatment) is decreased. Therefore, the Young's modulus is controlled by bending (second deformation treatment).

As the holding time in the heat treatment of the titanium-tantalum-based alloy is longer, the Young's modulus of the titanium-tantalum-based alloy is higher as shown in FIG. 7A. Therefore, the Young's modulus may be controlled by the heat treatment, in addition to, or in place of, bending of the angular plate 1 (second deformation treatment).

Figure 18:
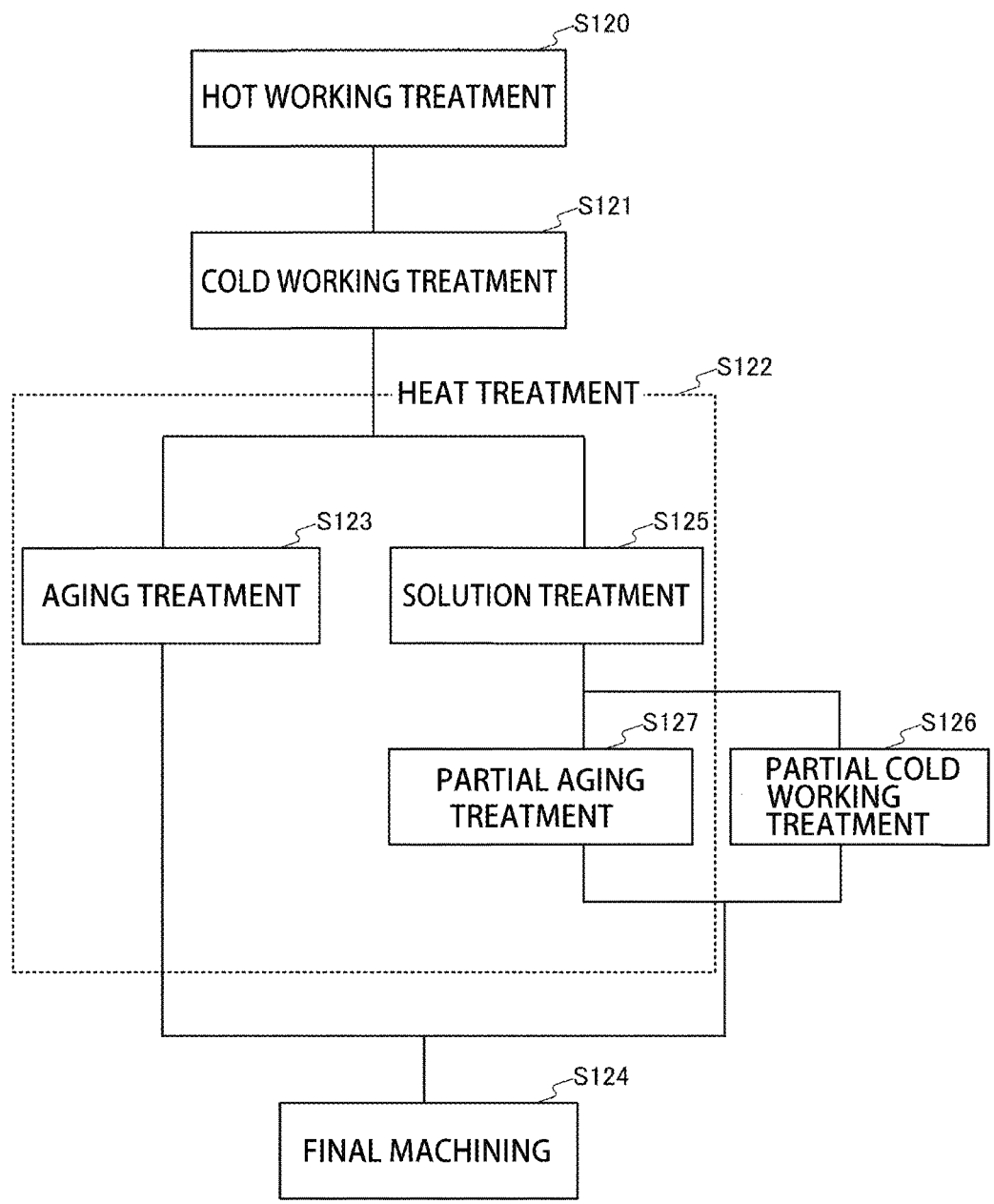
FIG. 18 is a flow chart showing a method for producing an implant in yet another embodiment of the present invention.

One example of a method for producing an implant in yet another embodiment of the present invention will be described below with reference to FIG. 18. One or more ingots of the titanium-tantalum-based alloy containing tin (Sn) are subjected to a hot working treatment (Step S120). After the hot working treatment of the ingots, an intermediate of an implant is obtained from the one or more ingots.

Specifically, in the hot working treatment of Step S120, the one or more ingots are heated to a predetermined temperature to form a plate having a predetermined thickness or a bar having a predetermined diameter. After the hot working treatment, the plate or the bar is obtained as the intermediate of the implant. When the one or more ingots are heated to a predetermined temperature in the hot working treatment, an effect that is the same as an effect obtained by a solution treatment of the one or more ingots may be obtained.

Subsequently, the intermediate of the implant having been subjected to the hot working treatment is subjected to a cold working treatment (Step S121). Examples of cold working may include bending, cutting, pressing, rolling, and forging. However, the cold working is not limited thereto, and may be another working. The cold working treatment in Step S121 corresponds to a molding treatment. By the cold working treatment in Step S121, the appearance shape of the implant is formed, and the reduction ratio of the intermediate of the implant may be controlled.

Next, the intermediate of the implant having been subjected to the cold working treatment is subjected to a heat treatment (Step S122). The heat treatment includes various aspects. For example, the whole of the intermediate of the implant having been subjected to the cold working treatment may be subjected to an aging treatment (Step S123). In this case, the hardness of the intermediate is increased overall. The intermediate of the implant having been subjected to the aging treatment is subjected to final machining (Step S124). Thus, the implant is completed.

For example, the intermediate of the implant having been subjected to the cold working treatment may be subjected to a solution treatment as the heat treatment (Step S125). By the solution treatment, a deposit from the titanium-tantalum-based alloy containing tin (Sn) constituting the intermediate of the implant is dissolved in a solid solution.

After the solution treatment, a part of the intermediate of the implant is subjected to a cold working (partial cold working) treatment (Step S126). By the partial cold working treatment, the reduction ratio of the part of the intermediate can be changed. An aspect in which the reduction ratio of the part of the intermediate is changed may include various aspects. Examples of the aspect may include an aspect in which the reduction ratio is continuously changed along the longitudinal direction of the intermediate of the implant and an aspect in which the reduction ratio is discontinuously changed along the longitudinal direction of the intermediate of the implant.

After the solution treatment, a part of the intermediate of the implant may be subjected to an aging treatment (partial aging treatment) (Step S127). By the partial aging treatment, the hardness of the part of the intermediate can be made higher than those of other parts.

The intermediate of the implant having been subjected to the partial cold working treatment in Step S126 or the partial aging treatment in Step S127 is subjected to final machining (Step S124). Thus, the implant is completed.

The implant and the method for producing an implant of the present invention are not limited to the above-described embodiments, and may be variously modified without departing from the scope of the present invention.

The entire disclosures of Japanese Patent Application Nos. 2016-193255, filed Sep. 30, 2016 and 2017-180994, filed Sep. 21, 2017 are expressly incorporated by reference herein.

What is claimed is:

1. An implant comprising at least partially an alloy containing titanium, tantalum, and tin, wherein
the alloy contains 15 at % to 27 at % of tantalum and 1 at % to 8 at % of tin, relative to an entire amount thereof taken as 100 at %, with a remaining part being titanium and unavoidable impurities.

2. The implant according to claim 1, at least partially comprising an elastically deforming part that is elastically deformable.

3. The implant according to claim 2, wherein the elastically deforming part includes a part having an increased reduction ratio as compared with other parts.

4. The implant according to claim 1, comprising a hardened part having an increased hardness as compared with other parts, the hardened part being formed by subjecting the part to a heat treatment.

5. The implant according to claim 1, wherein at least a part of the alloy is subjected to an aging treatment.

6. The implant according to claim 5, wherein the alloy is subjected to the aging treatment for a holding time of 30 hours or less.

7. The implant according to claim 1, wherein the implant repairs a bone.

8. The implant according to claim 7, comprising a part to be attached to an outer periphery of the bone, the part to be attached to the outer periphery of the bone being formed in a plate shape.

9. The implant according to claim 8, wherein the part to be attached to the outer periphery of the bone is fixed on the outer periphery of the bone with a screw member.

10. The implant according to claim 7, comprising a part to be attached to an inside of the bone.

11. The implant according to claim 7, comprising a part of penetrating insides of parts of a fractured bone.

12. The implant according to claim 11, wherein the part of penetrating the insides of the parts of the fractured bone is formed in a screw shape.

13. The implant according to claim 7, wherein the implant is at least partially formed in a screw shape.

14. The implant according to claim 7, wherein the implant is at least partially formed in a bar shape.

15. A method for producing an implant, comprising producing the implant from a material including an alloy containing titanium, tantalum, and tin, wherein the alloy contains 15 at % to 27 at % of tantalum and 1 at % to 8 at % of tin, relative to an entire amount thereof taken as 100 at %, with a remaining part being titanium and unavoidable impurities.

16. The method for producing an implant according to claim 15, comprising a deformation treatment step of deforming at least a part of the material.

17. The method for producing an implant according to claim 15, comprising an aging treatment step of subjecting at least a part of the material or at least a part of an intermediate that is formed during a process of producing the implant to an aging treatment.

18. The method for producing an implant according to claim 17, wherein the alloy is subjected to the aging treatment for a holding time of 30 hours or less.

19. The method for producing an implant according to claim 15, comprising a solution treatment step of subjecting at least a part of the material or at least a part of an intermediate that is formed during a process of producing the implant to a solution treatment.

20. The method for producing an implant according to claim 16, comprising a solution treatment step of subjecting at least a part of the material or at least a part of an intermediate that is formed during a process of producing the implant to a solution treatment, wherein
the solution treatment step is performed after the deformation treatment step.

21. The method for producing an implant according to claim 16, wherein the deformation treatment step is performed such that a reduction ratio of a part of the material is changed to a first reduction ratio, and a reduction ratio of at least a part of a rest of the material is changed to a second reduction ratio that is higher than the first reduction ratio.

22. The method for producing an implant according to claim 16:
wherein the material comprises two ingots including an alloy containing titanium and tantalum,
the deformation treatment step includes:
a first ingot deformation treatment step of changing a reduction ratio of at least a part of one of the ingots to a first reduction ratio; and
a second ingot deformation treatment step of changing a reduction ratio of at least a part of the other ingot to a second reduction ratio that is higher than the first reduction ratio,
the implant includes at least a first part and a second part,
the first part is formed from the ingot that has been subjected to the first ingot deformation treatment step, and
the second part is formed from the ingot that has been subjected to the second ingot deformation treatment step.

23. The method for producing an implant according to claim 16, wherein the implant is configured such that a part where a reduction ratio is changed in the deformation treatment step forms an elastically deforming part that is elastically deformable.

* * * * *